US009763954B2

(12) United States Patent
Soares Da Silva

(10) Patent No.: US 9,763,954 B2
(45) Date of Patent: Sep. 19, 2017

(54) THERAPEUTICAL USES OF ESLICARBAZEPINE

(71) Applicant: BIAL-PORTELA & CA, S.A., S. Mamede do Coronado (PT)

(72) Inventor: Patricio Manuel Vieira Araújo Soares Da Silva, Porto (PT)

(73) Assignee: BIAL—PORTELA & CA, S.A., S. Mamede do Coronado (PT)

( * ) Notice: Subject to any disclaimer, the term of this patent is extended or adjusted under 35 U.S.C. 154(b) by 243 days.

(21) Appl. No.: 14/134,843

(22) Filed: Dec. 19, 2013

(65) Prior Publication Data

US 2014/0309214 A1 Oct. 16, 2014

Related U.S. Application Data

(63) Continuation of application No. 12/522,535, filed as application No. PCT/PT2008/000002 on Jan. 14, 2008, now abandoned.

(30) Foreign Application Priority Data

Jan. 15, 2007 (GB) .................................. 0700773.5

(51) Int. Cl.
*A61K 31/55* (2006.01)
*A61K 45/06* (2006.01)

(52) U.S. Cl.
CPC .............. *A61K 31/55* (2013.01); *A61K 45/06* (2013.01)

(58) Field of Classification Search
CPC ........................................................ A61K 31/55
USPC ....................................................... 514/217
See application file for complete search history.

(56) References Cited

U.S. PATENT DOCUMENTS

| | | |
|---|---|---|
| 3,489,836 A | 1/1970 | Waring |
| 3,637,661 A | 1/1972 | Schindler |
| 3,642,775 A | 2/1972 | Schindler et al. |
| 4,076,812 A | 2/1978 | Allgeier et al. |
| 4,235,895 A | 11/1980 | Blattner et al. |
| 4,409,212 A | 10/1983 | Mondadori |
| 4,452,738 A | 6/1984 | Aufderhaar |
| 4,540,514 A | 9/1985 | Aufderhaar |
| 4,559,174 A | 12/1985 | Aufderhaar |
| 5,095,033 A | 3/1992 | Levy et al. |
| 5,368,865 A | 11/1994 | Asakura et al. |
| 5,466,683 A | 11/1995 | Sterling et al. |
| 5,472,714 A | 12/1995 | Bourquin |
| 5,496,564 A | 3/1996 | Asakura et al. |
| 5,624,945 A | 4/1997 | Bousseau et al. |
| 5,695,782 A | 12/1997 | Bourquin |
| 5,753,646 A | 5/1998 | Benes et al. |
| 5,827,819 A | 10/1998 | Yatvin et al. |
| 5,980,942 A | 11/1999 | Katzhendler et al. |
| 6,296,873 B1 | 10/2001 | Katzhendler et al. |
| 2001/0036943 A1 | 11/2001 | Coe et al. |
| 2002/0037926 A1 | 3/2002 | Lan |
| 2002/0147197 A1 | 10/2002 | Newman et al. |
| 2003/0055008 A1 | 3/2003 | Marcotte |
| 2003/0056896 A1 | 3/2003 | Jao et al. |
| 2003/0225002 A1 | 12/2003 | Livingstone |
| 2004/0038874 A1 | 2/2004 | Omoigui |
| 2004/0158060 A1 | 8/2004 | Learmonth |
| 2004/0162280 A1 | 8/2004 | Learmonth |
| 2004/0180816 A1 | 9/2004 | Loscher et al. |
| 2004/0185097 A1 | 9/2004 | Kannan et al. |
| 2004/0266754 A1 | 12/2004 | Learmonth |
| 2005/0004102 A1 | 1/2005 | Schmutz |
| 2006/0252745 A1 | 11/2006 | Almeida et al. |
| 2006/0252746 A1 | 11/2006 | Almeida et al. |
| 2007/0021356 A1 | 1/2007 | Cady |
| 2007/0142266 A1 | 6/2007 | Loscher et al. |
| 2010/0222327 A1 | 9/2010 | Almeida et al. |
| 2011/0319388 A1 | 12/2011 | de Almeida et al. |

FOREIGN PATENT DOCUMENTS

| | | |
|---|---|---|
| CA | 2 575 042 A1 | 11/1995 |
| CA | 2 356 460 A1 | 6/2000 |
| CA | 2 370 030 A1 | 10/2000 |
| CA | 2 446 160 A1 | 12/2002 |
| CA | 2 479 672 A1 | 10/2003 |
| CA | 2 494 660 A1 | 2/2004 |
| CA | 2 497 780 A1 | 4/2004 |
| CA | 2 498 890 A1 | 4/2004 |
| CA | 2 537 088 A1 | 3/2005 |
| CA | 2 543 829 A1 | 5/2005 |
| CA | 2 553 207 A1 | 8/2005 |
| DE | 2 011 045 | 10/1970 |
| EP | 0 435 826 A1 | 7/1991 |
| EP | 0 637 449 A1 | 2/1995 |
| EP | 0 646 374 A1 | 4/1995 |
| EP | 0 751 129 A1 | 1/1997 |
| EP | 1 239 832 B1 | 9/2002 |
| EP | 1 477 480 A1 | 11/2004 |
| GB | 864536 | 4/1961 |
| GB | 1 310 120 | 3/1973 |
| RU | 2079304 | 5/1997 |
| RU | 2178298 C1 | 1/2002 |
| RU | 2236224 C2 | 9/2004 |
| WO | WO 89/05642 A1 | 6/1989 |
| WO | WO 94/13298 A1 | 6/1994 |

(Continued)

OTHER PUBLICATIONS

US 5,753,645, 05/1998, Benás et al. (withdrawn)
Bialer, et al., "Progress Report on New Antiepileptic Drugs: A summary of the Eigth Eilat Conference (EILAT VIII)," Epilepsy Research (2007) 73, 1-8.
Berkow, R., Medical Manual—Diagnostic and Therapy, Medicine Handbook, M., Mir, 1997, vol. 1, p. 982.
Berkow, R., Medical Manual—Diaonostios and Therapy, Medicine Handbook, M., Mir, 1997, vol. 1, p. 982 (English-language translation).

(Continued)

*Primary Examiner* — Jennifer M Kim
(74) *Attorney, Agent, or Firm* — Finnegan, Henderson, Farabow, Garrett & Dunner, L.L.P.

(57) ABSTRACT

New applications of eslicarbazepine and eslicarbazepine acetate in the treatment of intractable conditions.

28 Claims, 5 Drawing Sheets

(56) References Cited

FOREIGN PATENT DOCUMENTS

| WO | WO 97/02250 A1 | 1/1997 |
|---|---|---|
| WO | WO 9702250 A1 | 1/1997 |
| WO | WO 97/38978 A1 | 10/1997 |
| WO | WO 98/17692 A1 | 4/1998 |
| WO | WO 98/35681 | 8/1998 |
| WO | WO 00/01416 A1 | 1/2000 |
| WO | WO 00/66096 A2 | 11/2000 |
| WO | WO 00/76942 A1 | 12/2000 |
| WO | WO 01/32183 A2 | 5/2001 |
| WO | WO 01/39779 A1 | 6/2001 |
| WO | WO 02/03915 A2 | 1/2002 |
| WO | WO 02/05799 A2 | 1/2002 |
| WO | WO 02/094774 A2 | 11/2002 |
| WO | WO 02092572 A1 | 11/2002 |
| WO | WO 02/098418 A1 | 12/2002 |
| WO | WO 02096881 A1 | 12/2002 |
| WO | WO 03/042182 A1 | 5/2003 |
| WO | WO 03/101428 A1 | 12/2003 |
| WO | WO 03/101430 A1 | 12/2003 |
| WO | WO 2004/014391 A1 | 2/2004 |
| WO | WO 2004/026314 A1 | 4/2004 |
| WO | WO 2004/031155 A1 | 4/2004 |
| WO | WO 2004/035041 A1 | 4/2004 |
| WO | WO 2004/069187 A2 | 8/2004 |
| WO | WO 2004/071152 A2 | 8/2004 |
| WO | WO 2004/071513 A1 | 8/2004 |
| WO | WO 2004/087161 A1 | 10/2004 |
| WO | WO 2004/087166 A1 | 10/2004 |
| WO | WO 2004/087168 A1 | 10/2004 |
| WO | WO 2004/100992 A2 | 11/2004 |
| WO | WO 2004099153 A1 | 11/2004 |
| WO | WO 2004/103348 A2 | 12/2004 |
| WO | WO 2005/020968 A2 | 3/2005 |
| WO | WO 2005/092290 | 10/2005 |
| WO | WO 2005/092294 | 10/2005 |
| WO | WO 2006005951 A1 | 1/2006 |
| WO | WO 2006054115 A1 | 5/2006 |
| WO | WO 2006075925 A2 | 7/2006 |
| WO | WO 2006120501 A1 | 11/2006 |
| WO | WO 2006121363 A1 | 11/2006 |
| WO | WO 2007012793 A1 | 2/2007 |
| WO | WO 2007094694 A1 | 8/2007 |
| WO | WO 2007117166 A1 | 10/2007 |
| WO | WO 2008088233 A1 | 7/2008 |
| WO | WO 2009054743 A1 | 4/2009 |
| WO | WO 2011031176 A1 | 3/2011 |

OTHER PUBLICATIONS

Berkow, R., Medical Manual—Diagnostics and Therapy, Medicine Handbook, M., Mir, 1997, vol. 1, Chap, 121, pp. 979-980 (3 pages).
Berkow, R., Medical Manual—Diagnostics and Therapy, Medicine Handbook, M., Mir, 1997, Vol, 1, Chap. 121. pp. 979-980 (English-language translation) (4 pages).
Medical Consultation & New Remedies, 1982, vol. 18, No. 2, pp. 245-250 (with partial translation).
English-language translation of Medical Consultation & New Remedies, 1982, vol. 18, No. 2, pp. 245-250.
English-language translation of Russian Application No. RU 2178298 C1, published Jan. 20, 2002 (6 pages).
English-language translation of Russian Application No. RU 2236224 C2, published Sep. 20, 2004 (3 pages).
Abbott, N. Joan, et al., "Drug resistence in epilepsy: the role of the blood-brain barrier," Mechanisms of Drug Resistance in Epilepsy: Lessons From Oncology, 2002, pp. 38-53, Novartis Foundation.
Almeida, L., et al., "Effect of gender on the pharmacokinetics of eslicarbazepine acetate (BIA 2-093), a new voltage-gated sodium channel inhibitor," Epilepsia, 26th IEC Proceedings, 2005, vol. 46, Suppl, No. 6, pp. 282-283.

Almeida, L., et al., "Pharmacokinetic profile of BIA 2-093, a putative new antiepileptic drug, after single and multiple administration in human healthy volunteers," Epilepsia, 5th ECE Proceedings, 2002, vol. 43, Suppl. No. 8, pp. 146-147.
Almeida, Luis, et al., "Eslicarbazepine Acetate", The Treatment of Epilepsy, 2009, pp. 485-498 plus cover page and publishing information, 3rd Edition, Blackwell Publishing.
Almeida, Luis, et al., "Eslicarbazepine Acetate (BIA 2-093)," Neurotherapeutics: The Journal of the American Society for Experimental NeuroTherapeutics, Jan. 2007, vol. 4, No. 1, pp. 88-96, The American Society for Experimental NeuroTherapeutics, Inc.
Almeida, Luis, et al., "Pharmacokinetics, Efficacy, and Tolerability of Esilcarbazepine Acetate in Chiidren and Adolescents With Epilepsy", The Journal of Clinical Pharmacology, 2008, pp. 966-977 plus 1 page cover, vol. 48, Sage Publications.
Almeida, Luis, et al., "Safety, tolerability and pharmacokinetic profile of BIA 2-093, a novel putative antiepileptic agent, during first administration to humans," Drugs R&D, 2003, vol. 4, No. 5, ppp. 269-284, Adis Data information B. V.
Almeida, Luis, et al.. "Safety, tolerability and pharmacokinetic profile of BIA 2-093, a novel putative antiepileptic, in a rising multiple-dose study in young healthy humans," Journal of Clinical Pharmacology, 2004, vol. 44, pp. 906-918, The Americans College of Clinical Pharmacology.
Almeida, Luis, et al "Single-dose and steady-state pharmacokinetics of eslicarbazepine acetate (BIA 2-093) in healthy elderly and young subjects," Journal of Clinical Pharmacology, 2005, vol. 45, pp. 1062-1066, The American College of Clinical Pharmacology.
Alves, Gilberto, et al,, "Plasma-Brain Distribution of LiCarbazepine Enantiomers in Mice on Steady-State Conditions", Thirty-Eighth Annual ACCP Meeting Abstracts p. 1111, Sep. 2009.
Alves, Gilberto, et al., "Stereoselective Disposition of S-and R-Lioarbazepine in Mice", Chirality, 2008, pp. 796-804. vol. 20, Wiley-Liss, Inc.
Ambrosio et al. Mechanism of action of carbamazepine and its derivatives, oxcarbazepine, BIA 2-093, and BIA 2-024, Neurochemical Research, vol. 27, Nos. 1/2 Feb. 2002 pp. 121-130.
Ambrosio, Antonio F., et al., "Neurotoxic/neuroprotective profile of carbamazepine, oxcarbazepine and two new putative antiepileptic drugs, BIA 2-093 and BIA 2-024," European Journal of Pharmacology, 2000, vol. 406, pp. 191-201, Elsevier.
Aronica, E., et al,,. "Expression and cellular distribution of multidrug transporter proteins in two major causes of medically intractable epilepsy: focal cortical dysplasia and glioneuronal tumors," Neuroscience, 2003, vol. 118, pp. 417-429, Elsevier Science Ltd.
Aronica, Eleonora, et al., "Expression and cellular distribution of multidrug resistance-related proteins in the hippocampus of patients with mesial temporal lobe epilepsy," Epilepsia, 2004, vol. 45, No. 5, pp. 441-451, International League Against Epilepsy.
Bazil, Carl W., "Epilepsy and sleep disturbance," Epilepsy and Behavior, 2003, vol. 4, pp. S39-S45, Elsevier, Inc.
Benes, Jan, et al., "Anticonvulsant and sodium channel-blocking properties of novel 10,11-dihyrdo-5H-dibenz[b,f]azepine-5-carboxamide derivatives," Journal of Medical Chemistry, 1999, vol. 42, pp. 2582-2587, American Chemical Society.
Ben-Menachem, E., et al., "Esilcarbazepine Acetate as Adjunctive Therapy in Adult Patients with Partial Epilepsy", Epilepsy Research, 2010, pp. 1-8, Elsevier B.V.
Betts, Tim, et al., "Clinical experience of marketed Levetiracetam in an epilepsy clinic—a one year follow up study," Seizure, 2003, vol. 12, pp. 136-140, BEA Trading Ltd.
Bialer, Meir, et al., "Key Factors in the Discovery and Development of New Antiepileptic Drugs", Nature Reviews, Drug Discovery, Jan. 2010, pp. 68-82, vol. 9, Macmillian Publishers Limited.
Bialer, Meir, et al., "Progress report on new atiepileptic drugs: a summary of the Seventh Eilat Conference (EILAT VII)," Epilepsy Research, 2004, vol. 61, pp. 1-48, Elsevier.
Clinkers, Ralph, et al., "Quantitative in vivo microdialysis study on the influence of multidrug transporters on the blood-brain barrier passage of oxcarbazepine: concomitant use of hippocampal monoamines as pharmacodynamic markers for the anticonvulsant activity," The Journal of Pharmacology and Experimental Therapeutics, 2005, vol. 314, No. 2, pp. 725-731, The American Society for Pharmacology and Experimental Therapeutics, XP008091105.

(56) References Cited

OTHER PUBLICATIONS

Cretin, Benjamin, et al., "Adjunctive Antiepileptic Drugs in Adult Epilepsy: How the First Add-On Could be the Last", Expert Opin. Phamacother., 2010, pp. 1053-1067, vol. 11, No. 7, Informa UK Ltd.

Czapinski, P., et al., "Efficacy and Safety of Eslicarbazepine Acetate (ESL) as Add-On Treatment in Audlts with Refractory Partial-Onset Seizures: BIA-2093-301 Study", Epilepsia, 2008, pp. 428, vol. 49, Suppl. 7.

"Diagnosis and Management of Epilepsy in Adults", Apr. 2003, 54 pages. Scottish Intercollegiate Guidelines Network.

Dombrowski, Stephen M., et al., "Overexpression of multiple drug resistance genes in endothlial cells from patients with refractory epilepsy," Epilepsia, 2001, vol. 42, No. 12, pp. 1501-1506, International League Against Epilepsy.

Elger, C., et al., "Efficacy and Safety of Eslicarbazepine Acetate as Add-On Treatment in Patients with Partial-Onset Seizures: Pooled Analysis of Three Double-Blind Phase III Clinical Studies", Epilepsia, 2008, pp. 428-429 vol. 49, Suppl. 7.

Faigle, Johann W., et al., "Metabolic characteristics of oxcarbazepine (trileptal) and their beneficial implications for enzyme induction and drug interactions," Behav Neuro, 1990, vol. 3, Suppl. No. 1, pp. 21-30.

Feldmann, K. F., "Pharmacokinetics and metabolism of GP 47 680, a compound related to cabamazepine, in animals and man," Advances in Epileptology, 1978, pp. 290-294, Swets & Zeitlinger B.V.

Feldmann, K. F., et al., "Pharmacokinetics and metabolism of GP 47 779, the main human metabolite of oxcarbazepine (GP 47 680) in animals and healthy volunteers," Advances in Epileptology: The Xilth Epilepsy International Symposium, 1981, pp. 89-96, Raven Press Books Ltd.

Flesch. G., et al., "Determination of the R- (−) and S- (+) enantiomers of the monohydroxylated metabolite of oxcarbazepine in human plasma by enantipselective high-performance liquid chromatography," Journal of Chromatography, 1992, vol. 581, pp. 147-151, Elsevier Science Publishers B.V.

Foreign communication from a related counterpart application—International Preliminary Report on Patentability, PCT/PT2008/000002, 8 pages, Jul. 21, 2009.

Foreign communication from a related counterpart application—International Search Report and Written Opinion, PCT/PT2008/000002, 14 pages, May 21, 2006.

French, J.A., et al., "Efficacy and tolerability of the new antiepileptic drugs II: Treatment of refractory epilepsy", Neurology; 2004, pp. 1261-1273, vol. 62, AAN Enterprises, Inc.

French, Jacqueline, "Refractory Epilepsy: One Size Does Not Fit All," Epilepsy Currents, vol. 6, No. 6, pp. 177-180, Nov./Dec. 2006, Blackwell Publishing, Inc. American Epilepsy Society.

Fuseau, E., et al., "Population Pharmacokinetics of Eslicarbazepine Acetate in Adult Patients with Refractory Partial Seizures", Epilepsia, 2008, pp. 432. vol. 49, Suppl 7.

Gabbai, A.A., et al., "Long-Term Treatment of Partial Epilepsy with Eslicarbazepine Acetate (ESL): Results of a One-Year Open-Label Extension of Study BIA-2093-302", Epilepsia, 2008, pp. 432-433 vol. 49, Suppl. 7.

Gerk, Philip M., et al., "Regulation of expression of the multidrug resistance-associated protein 2 (MRP2) and its role in drug disposition," The Journal of Pharmacology and Experimental Therapeutics, 2002, vol. 302. No. 2, pp. 407-415. The American Society for Pharmacology and Experimental Therapeutics.

Gil-Nagel., Antonio, et al., "Efficacy and Safety of Esilcarbazepine Acetate (ESL) as Add-On Treatement in Adults with Refractory Partial-Onset Seizures: BIA-2093-303 Study", Epilepsia, 2008, pp. 433-434, vol. 49, Suppl. 7.

Hainzl, Dominik, et al., "Metabolism of two new antiepileptic drugs and their principal metabolites S(+)- and R(−)-10,11-dihyrdo-10-hydroxy carbamazepine," Epilepsy Research, 2001, vol. 44, pp. 197-206, Elsevier Science B.V.

Kortekaas, Rudie, et al., "Blood brain baffler dysfunction in parkinsonian rnidbrain in vivo," Annals of Neurology Feb. 2005, vol. 57. No. 2, pp. 176-179, American Neurological Association.

Kwan, Patrick, et al., "Early identification of refractory epilepsy," The New England Journal of Medicine, Feb. 3, 2000, vol. 342, No. 5, pp. 314-319, Massachusetts Medical Society.

Kwan, Patrick, et al., "Potential role of drug transporters in the pathogenesis of medically intractable epilepsy," Epilepsia, 2005, vol. 46 No. 2, pp. 224-235, International League Ageinst Epilepsy.

Lopes-Lima, J., et al., "Long-Term Treatment of Partial Epiiepsy with Eslicarbazepine Acetate (ESL): Results of a One-Year Open-Label Extention of Study BIA-2093-303", Epilepsia, 2008, pp. 441-442, vol. 49, Suppl. 7.

Loscher, Wolfgang, et al., "Drug resistance in brain diseases and the role of drug efflux transporters," Nature Reviews Neuroscience, Aug. 2005, vol. 6, pp. 591-602. Nature Publishing Group.

Loscher, Wolfgang, et al., "New horizons in the development of antiepileptic drugs: the search for new targets," Epilepsy Research, 2004, vol. 60, pp. 77-159, Elsevier.

Loscher, Wolfgang, et al., "Role of drug efflux transporters in the brain for drug disposition and treatment of brain diseases," Progress in Neurobiology 2000 vol. 76 pp. 22-76, Elsevier Ltd.

Maia, J., et al., "BIA 2-093 as add-on therapy for refractory partial epilepsy in adults," Epilepsia, 6th ECE Proceedings, 2004, vol. 45, Suppl, No. 3. p. 158 + 1 pg.

Maia, J., et al., "Effect of eslicarbazepine acetate (BIA 2-093) on the steady-state pharmacokinetics of digoxin in healthy subjects," Epilepsia, 26th IEC Proceedings, 2005, vol. 46, Suppl. No. 6, p. 283, XP008091102.

Marchi, Nicola, et al., "A pilot study on brain-to-plasma partition of 10,11-dyhydro-10-hydroxy-5H-dibenzo(b,f)azepine-5-carboxamide and MDR1 brain expression in epilepsy patients not responding to oxcarbazepine," Epilepsia, 2005, vol. 46, No. 10, pp. 1613-1620, International League Against Epilepsy, XP008091107.

Marchi, Nicola, et al., "Significance of MDR1 and multiple drug resistance in refractory human epileptic brain," BMC Medicine, 2004, vol. 2, No. 37, 10 pages, BioMed Central.

May, The Odor W., et al., "Clinical pharmacoidnetics of oxcarbazepine," Clinical Pharmacokinetics, 2003, vol. 42, No. 12, pp. 1023-1042, Adis Data Information B.V.

McCormack, Paul L., et al., "Eslicarbazepine Acetate", CNS Drugs, 2009, pp. 71-79, vol. 23, No. 1, Adis Data Information BV.

Mestre, Tiago, et al.. "Esiicarbazepine Acetate: A New Option for the Treatment of Focai Epilepsy", Expert Opin, Investig Drugs, 2009, pp. 221-229, vol. 18, No. 2, Informa.

Mohan Raj, Rajiv, et al., "Pharmacological outcomes in newly diagnosed epilepsy," Epilepsy and Behavior, 2005, vol. 6, pp. 382-387, Elsevier Inc.

Owen, Richard T "Eslicarbazepine Acetate: A Novel Agent for the Adjunctive Treatment of Epilepsy", Drugs of Today, 2010 pp, 23-31, vol. 46, No. 1, Proses Scoemce. S.A.U.

Patsalos, Philip N., et al., "Clinically important drug interactions in epilepsy: general features and interactions between antiepileptic drugs", Neurology, Jun. 2003, pp. 347-356, vol. 2, The Lancet.

Perucca, E., et al., "Pharmaconkinetics of Eslicarbazepine Acetate at Steady-State in Adults with Epilepsy", Epilepsia, 2009, p. 196, vol. 50, Suppl. 4.

Potschka, Heidrun, et al., "In vivo evidence for p-glycoprotein-mediated transport of phenytoin at the blood-brain barrier of rats," Epilepsia, 2001, vol. 42, No. 10, pp. 1231-1240, International League Against Epilepsy.

Potschka, Heidrun, et al., "Inhibition of multidrug transporters by verapamil or probenecid does not alter blood-brain barrier penetration of levetiracetarn in rats," Epilepsy Research, 2004, vol. 58, pp. 85-91, Elsevier B.V.

Potschka, Heidrun, et al., "Multidrug resistance protein MRP2 contributes to biood-brain barrier function and restricts antiepileptic drug activity," The Journal of Pharmacology and Experimental Therapeutics, 2003, vol. 306. No. 1, pp. 124-131, The American Society for Pharmacology and Experimental Therapeutics.

Potschka, Heidrun, et al., "P-glycoprotein and multidrug resistance-associated protein are involved in the regulation of extracellular levels of the major antiepileptic drug carbamazepine in the brain," Neuropharmacology and Neurotoxicology, Nov. 16, 2001, vol. 12, No. 16, pp. 3557-3560, NeuroReport.

(56) References Cited

OTHER PUBLICATIONS

Potschka, Heidrun. et al., "P-glycoprotein-mediated efflux of phenobarbital, lamotrigine, and felbamate at the blood-brain barrier: evidence from microdialysis experiments in rats," Neuroscience Letters, 2002. vol. 327, pp. 173-176, Elsevier Science Ireland Ltd.
Racine, Ronald, et al., "Modification of seizure activity by electrical stimulation: III. mechanisms," Electroencephalography and Clinical Neurophysiology, 1972, vol. 32, pp. 295-299, Elsevier Publishing Company.
Rambeck, Bernhard, et al., "Comparison of Brain Extracellular Fluid, Brain Tissue, Cerebrospinal Fluid, and Serum Concentrations of Antiepileptic Drugs Measured Intraoperatively in Patients with Intractable Epilepsy," Epilepsia, vol. 47, No. 4, pp. 681-694, 2006, Blackwell Publishing, Inc., International League Against Epilepsy.
Rauchenzauner, Markus, et al., "Update on Treatment of Partial Onset Epilepsy: Role of Eslicarbazepine", Neuropsychiatric Disease and Treatment, 2010, pp. 723-730, vol. 6. Dove Medical Press Ltd.
Ray et al. Treatment options and paradigms in childhood temporal lobe epilepsy. Expert Review of Neurotherapeutics, No. 2003. vol. 5, No. 6, pp. 785-801. Abstract.
Rizzi, Massimo, et al., "Limbic seizures induce p-glycoprotein in rodent brain: functional implications for pharmacoresistance," The Journal of Neuroscience, Jul. 15, 2002, vol. 22 No. 14, pp. 5833-5839.
Scheffer, George L., et al., "Drug resistance molecules lessons from oncology," Novartis Foundation Symposium 243, 2002, pp. 19-37, Wiley, Chichester.
Schinkel, Alfred H., et al., "Mammalian drug efflux transporters of the ATP binding cassette (ABC) family: an overview," Advanced Drug Delivery Reviews, 2003 vol. 55, pp. 3-29, Elsevier Science B.V.
Schinkel, Alfred H., et al., "P-glycoprotein in the blood-brain barrier of mice influences the brain penetration and pharmacological activity of many drugs," Journal of Clinical Investigation, Jun. 1996, vol. 97, No. 11, pp. 2517-2524, The American Society for Clinical Investigation, Inc.
Schmidt, D., et al., "Recommendations on the clinical use of oxcarbazepine in the treatment of epilepsy: a consensus view," Acta Neurologica Scandinavica, 2001, vol. 104, pgs. 167-170, Munksgaard.
Schmidt, Dieter, et al., "Drug resistance in epilepsy: putative neurobiologic and clinical mechanisms," Epilepsia, 2005, vol. 46, No. 6, pp. 858-877, International League Against Epilepsy.
Schultz, H., et al., "The metabolism of 14C-oxcarbazepine in man," Xenobiotica, 1986, vol. 16, No. 8. pp. 769-778.
Shneker, Bassei F., et al., "Epilepsy", Jul. 2003, pp. 426-478, vol. 49, Mosby, Inc.
Shorvon, Simon, "Oxcarbazepine: a review," Seizure, 2000, vol. 9 pp. 75-79, BEA Trading Ltd.
Sills. Graeme J., et al., "P-glycoprotein-rnediated efflux of antiepileptic drugs: preliminary studies in mdrl a knockout mice," Epilepsy and Behavior, 2002, vol. 3, pp. 427-432 Academic Press.
Sisodiya, S.M., et al., "Drug resistance in epilepsy: expression of drug resistance proteins in common causes of refractory epilepsy," Brain. 2092. vol. 125 pp. 22-31 Oxford University Press.
Sisodiya, Sanjay M., "Mechanisms of antiepileptic drug resistance," Current Opinion in Neurology, 2003, vol. 16, pp. 197-201, Lippincott Williams & Wilkins.
Soares-Da-Silva, P., "BiA 2-093," Epilepsy Research, 2004, vol. 61, pp. 4-6.
Soares-Da-Silva, Patricio, et al., "Effect of age and gender on the pharmacokinetics of eslicarbazepine acetate," Epilepsia, AES Proceedings, 2005, vol. 46, Suppl. No. 8, pp. 216-217, XP018091113.
Sperling, Michael R., "The consequences of uncontrolled epilepsy," CNS Spectrums, Feb. 2004, vol. 9, No. 2, pp. 98-109.
Stephen, Linda J., et al., "Pharmacological outcomes in older people with newly diagnosed epilepsy." Epiiepsy and Be0havior, 2006, vol. 8, pp. 434-437, Elsevier Inc.
Summers, Monica A., et al., "Use of verapamil as a potential p-glycoprotein inhibitor in a patient with refractory epilepsy," The Annals of Pharmacotherapy, Oct. 2004 vol. 38, pp. 1631-1634.
Tartara, A., et al., "The pharmacokinetics of oxcarbazepine and its active metabolite 10-hydroxy-carbazepine in healthy subjects and in epileptic patients treated with phenobarbitone or valproic acid," British Journal of Clinical Pharmacology, 1993, vol. 36, pp. 366-368.
Tishler, David M., "MDR1 gene expression in brain of patients with medically intractable epilepsy," Epilepsia, 1995, vol. 36, No. 1, pp. 1-6, International League Against Epilepsy.
Van Vliet, Erwin A., et al., "Inhibition of the Multidrug Transporter P-Glycoprotein Improves Seizure Control in Phenytoin-treated Chronic Epileptic Rats," Epilepsia, vol. 47, No. 4, pp. 672-680, 2006, Blackwell Publishing, Inc., Internationai League Against Epilepsy.
Van Vliet, Erwin, et al., "Selective and persistent upregulation of mdr1b mRNA and p-glycoprotein in the parahippocampal cortex of chronic epileptic rats," Epiiepsy Research, 2004, vol. 60, pp. 203-213, Elsevier B.V.
Vaz Da Silva, Manuel, et al., "Effect of Eslicarbazepine Acetate on the Pharmacokinetics of Digoxin in Healthy Subjects", Fundamental & Clinical Pharmacology, 2009, pp. 509-514, vol. 23, The Authors Journal compilation.
Vohora, D., et at. "Recent Advances in Adjunctive Therapy for Epilepsy: Focus on Sodium Channel Blockers as Third-Generation Antiepileptic Drugs". Drugs of Today, 2010, pp. 265-277, vol. 46, No. 4, Prous Science S.A.U.
Volk, H. A., et al., "Increased expression of the multidrug transporter p-glycoprotein in limbic brain regions after amygdala-kindled seizures in rats," Epilepsy Research, 2004, vol. 58, pp. 67-79, Elsevier B.V.
Volk, H. A., et al., "Neuronal expression of the drug efflux transporter p-glycoprotein in the rat hippocampus after limbic seizures " Neuroscience, 2004, vol. 123, pp. 751-759, Elsevier Ltd.
Volosov; Andrew, et al., "Enantioselective pharmacokinetics of 10-hydroxycarbazepine after oral administration of oxcarbazepine to healthy Chinese subjects," Clinical Pharmacology and Therapeutics, Dec. 1999, vol. 66, No. 6, pp. 547-553.
Wheeler-Aceto, Helen, et al., "Standardization of the rat paw formalin test for the evaluation of analgesics," Psychopharmacology, 1991, vol. 104, pp. 35-44, Springer-Verlag.
Zakrzweska, J. M., et al. "Oxcarbazepine: a new drug in the management of intractable trigeminal neuralgia," Journal of Neurology, Neurosurgery and Psychiatry. 1939, vol. 52, pp. 472-476.
Kondratieva, T. C. et al., "Drug Formulation Technology," Technology of Dosage Forms, 1991, vol. 1, p. 97.
English-language translation of Kondratieva, T.C. et al., "Drug Formulation Technology," Technology of Dosage Forms, 1991, vol. 1, p. 97.
"DSM-IV Criteria for Bipolar Disorder," Diagnostic and Statistical Manual of Mental Disorders, 4th Ed., 1994, American Psychiatric Association, pp. 350-363.
"Oxcarbazepine," The Lancet, 196-198 (1989).
"Oxcarbazepine for Epilepsy—A Useful New Choice?", Drug & Therapeutics Bulletin, vol. 40, No. 6, pp. 46-48, Jun. 2002.
"Oxcarbazepine," New Medicines on the Market, UK Medicines Information, Monograph No. 4/00/15, pp. 1-5, Aug. 2000.
"Panel Discussion," Epilepsia, 40 (Suppl. 6): S73-S74 (1999).
"Strategies to Control Pain in Older Persons: Highlights of Recent Guidelines," Consultant, vol. 42(11): 1373-1376 (2002).
"The Merck Manual," 1406-1408, (1999).
Abraham, G. et al., "Possible Interaction of Clozapine and Lisinopril," Am. J. Psychiatry, 158:6, p. 969, Jun. 2001.
Albani, F. et al., "Oxcarbazepine—Interactions with Other Drugs," Antiepileptic Drugs, 5th ed., pp. 466-469, 2002.
Almeida, L. et al., "A Double-Blind, Add-On, Placebo-Controlled Exploratory Trial of Eslicarbazepine Acetate in Patients with Partial-Onset Seizures," Epilepsia, AES Proceedings, 2005, Abstract 2.229, p. 167-168.

(56) References Cited

OTHER PUBLICATIONS

Almeida et al., "Pharmacokinetic Profile of BIA 2-093, A Punitive New Antiepilepic Drug After Single and Multiple Administration in Human Healthy Volunteers," Epilepsia, vol. 43, suppl 8, p. 460, 2002.

Almeida, L. et al. "Effect of gender on the eslicarbazepine acetate pharmacokinetics in health subjects," J. Clin Pharmacology, poster at 26th International Epilepsy Congress (2005).

Almeida, L. et al., "Once-Daily versus twice-daily therapy with the novel antiepileptic drug eslicarbazepine acetate," Department of Research and Development, BIAL (Portela & Ca SA), S Mamede do Coronado, Portugal.

Almeida, L. et al., "Safety, Tolerability and Pharmacokinetic Profile of BIA 2-093, a Novel Putative Antiepileptic Agent, during First Administration to Humans," Drugs R&D 4(5); pp. 269-284, (2003).

Ambrósio, A. et al., "Inhibition of glutamate release by BIA 2-093 and BIA 2-024, two novel derivatives of carbamazepine, due to blockade of sodium but not calcium channels," Biochemical Pharmacology 61:1271-1275 (2001).

Ambrosio, A. et al., "Mechanisms of Action of Carbamazepine and Its Derivatives, Oxcarbazepine, BIA 2-093, a vd BIA 2-024," Neurochemical Research, vol. 27, Nos. 1/2, Feb. (2002), pp. 121-130.

Araújo, I. et al., "Neurotoxicity Induced by Antiepileptic Drugs in Cultured Hippocampal Neurons: A Comparative Study between Carbamazepine, Oxcarbazepine, and Two New Putative Antiepileptic Drugs, BIA 2-024 and BIA 2-093," Epilepsia 45 (12); pp. 1498-1505 (2004).

Auberson, Y. et al., "N-Phosphonoalkyl-5-aminomethylquinoxaline-2,3-diones: In Vivo Active AMPA and NMDA(Glycine) Antagonists," Bioorg. Med. Chem. Lett. 9, 249-254 (1999).

Augusteijn, R. et al., "Oxcarbazepine (Trileptal, OXC)-Dose-Concentration Relationship in Patients with Epilepsy," Acta. Neurolo. Scan., Proceedings of the Northern European Epilepsy Symposium, 37:82(S133), G10, 1990.

Baruzzi, A. et al., "Oxcarbazepine: Pharmacokinetic Interactions and Their Clinical Relevance," Epilepsia 35 (Suppl. 3), S14-S19 (1994).

Beelen, AP et al., "Asymptomatic QTc Prolongation associated with quetiapine fumarate overdose in a patient being treated with risperidone," Human & Experimental Toxicology, No. 20, pp. 215-219 (2002).

Benes, F. et al., "GABAergic Interneurons: Implications for Understanding Schizophrenia and Bipolar Disorder," Neuropsychopharmacology,vol. 25, No. 1, pp. 1-27 (2001).

Berk, M. et al., "Olanzapine compared to lithium in mania: a double-blind randomized controlled trial." Int Clin Psychopharmacol, 14: 339-343 (1999).

Beydoun, A. et al., "Oxcarbazepine," Expert Opin. Pharmacother. 3(1), pp. 59-71 (2002).

Beydoun, A., "Postherpetic Neuralgia: Role of Gabapentin and Other Treatment Modalities," Epilepsia, vol. 40 (Suppl. 6), S51-S56 (1999).

Bhana, N. et al. "Olanzapine: A Review of its Use in the Treatment of Bipolar I Disorder." CNS Drugs, 15: 871-904 (2001).

Bialer, "New Antiepileptic Drugs Currently in Clinical Trials: Is There a Strategy in Their Development," Therapeutic Drug Monitoring (2002) 24: 85-90.

Bialer, M., "Oxcarbazepine—Chemistry, Biotransformation, and Pharmacokinetics," Antiepileptic Drugs, 5th ed., 459-465, 2002.

Bialer, M., "Pharmacokinetic Evaluation of Sustained Release Formulations of Antiepileptic Drugs," Clinical Pharmacokinet. 22(1): pp. 11-21, (1992).

Bill, P.A. et al., "A Double-Blind Controlled Clinical Trial of Oxcarbazepine Versus Phenytoin in Adults with Previously Untreated Epilepsy," Epilepsy Research, 27, pp. 195-204, (1997).

Bonifacio, M.J. et al., "Laboratory Research: Interaction of the Novel Anticonvulsant, BIA 2-093, with Voltage-Gated Sodium Channels: Comparison with Carbamazepine," Epilepsia, 42(5):600-608 (2001).

Bonifácio, M.J. et al., "Interaction of the Novel Anticonvulsant, BIA 2-093, with Voltage-Gated Sodium Channels: Comparison with Carbamazepine," Epilespsia, 42(5):600-608 (2001).

Borges et al., "Urban Prevalence of Epilepsy: Populational Study in San Jose do Rio Preto, a medium-sized city in Brazil," Arq Neuropsiquiatr (2004) 62(2-A): pp. 199-205.

Borowicz K. et al., "Interaction of GYKI 52466, A Selective Non-Competitive Antagonist of AMPA/Kainate Receptors, with Conventional Antiepileptic Drugs in Amygdala-kindled Seizure in Rats," Polish Journal of Pharmacology, 53: pp. 101-108 (2001).

Borowicz, K. et al., "The non-competitive AMPA/kainate receptor antagonist, GYKI 52466, potentiates the anticonvulsant activity of conventional antiepileptics," European Journal of Pharmacology 281, 319-326 (1995).

Cabrera, J. et al., "Kombinierte rezidiv-prophylaktische Behandlung der manisch-depressiven Erkrankung mit Lithium and Carbamazepin oder Oxcarbazepin," Der Nervenarzt, 58:245-249 (1987).

Cabrera, J.F. et al., "Long-term randomized Clinical Trial on Oxcarbazepine vs Lithium in Bipolar and Schizoaffective Disorders: Preliminary Results," Pharmacopsychiat. 19, 282-283 (1986).

Calabrese, J., "Lamotrigine and Clozapine for Bipolar Disorder," Am. J. Psychiatry, v. 157, No. 9, 1523 (2000).

Carroll, B.T. et al. "Loading Strategies in Acute Mania," CNS Spectrums, 6: 919-922, 930 (2001).

Christe, W. et al., "A Double-Blind Controlled Clinical Trial: Oxcarbazepine Versus Sodium Valproate in Adults with Newly Diagnosed Epilepsy," Epilepsy Research, 26, p. 451-460, (1997).

Collins, R.J. et al., "Extended Release Formulations of Anticonvulsant Medications," CNS Drugs 2000, Sep. 14(3): p. 203-212.

Cookson, J. "Toward a Clinical Understanding of Bipolar Disorders: Classification and Presentation," Epilepsia, 46 (Suppl. 4); 3-7, 2005.

Cramer et al., "Quality of Life Improvement with conversion to lamotrigine monotherapy," Epilepsy & Behavior (2004), 5(2): 224-230.

Cunha, R. et al., "Effects of Carbamazepine and Novel 10,11-Dihydro-5H-Dibenz[b,f]Azepine-5-Carboxamide Derivatives on Synaptic Transmission in Rat Hippocampal Slices," Pharmacology & Toxicology, 90:208-213 (2002).

Czuczwar, S. et al., "LY 300164, a novel antagonist of AMPA/kainate receptors, potentiates the anticonvulsive activity of antiepileptic drugs," European Journal of Pharmacology, 359, 103-109 (1998).

Czuczwar, S. et al., "The New Generation of GABA Enhancers: Potential in the Treatment of Epilepsy," CNS Drugs 15(5), 339-350 (2001).

Dam, M. "Summing up of the success so far gained through choice of drugs or combination of drugs," Acta Neurologica Scandinavica, 19-22 (1984).

Dam, M. et al., "A Double-Blind Study Comparing Oxcarbazepine and Carbamazepine in Patients with Newly Diagnosed, Previously Untreated Epilepsy," Epilepsy Res., 3(1989), pp. 70-76.

Dean, B. et al., "A change in the density of [$^3$H] flumazenil, but not [$^3$H]muscinmol binding, in Brodmann's Area 9 from subjects with bipolar disorder," Journal of Affective Disorders 66, 147-158 (2001).

Deckers, C. et al., "Selection of Antiepileptic Drug Polytherapy Based on Mechanisms of Action: The Evidence Reviewed," Epilepsia 41(11); 1364-1374 (2000).

Dembowski, C. et al., "Successful Antimanic Treatment and Mood Stabilization with Lamotrigine, Clozapine, and Valproate in a Bipolar Patient after Lithium-induced Cerebellar Deterioration," Pharmacopsychiatry, v. 36, pp. 83-86 (2003).

Dickenson, A.H. et al., "The Pharmacology of Excitatory and Inhibitory Amino Acid-Mediated Events in the Transmission and Modulation of Pain in the Spinal Cord," Gen. Pharmac. vol. 28, No. 5, pp. 633-638 (1997).

(56) References Cited

OTHER PUBLICATIONS

Dietrich, D.E. et al., "Oxcarbazepine in Affective and Schizoaffective Disorders," Pharmacopsychiatry, vol. 34, 242-250 (2001).
Dost, R. et al., "ELB139: a new anxiolytic compound with potent effects in rodent models for generalised and focal seizures," Abstracts from the 6th European Congress on Epileptology, Journal of the International League Against Epilepsy, Epilepsia, vol. 45, Suppl. 3, pp. 116, p. 242, 2004.
Duby, J. et al., "Diabetic Neuropathy: An Intensive Review," AM J Health-Syst Pharm, vol. 61, 160-176 (2004).
Dursun, S.M. et al., "Clozapine Plus Lamotrigine in Treatment-Resistant Schizophrenia," Arch Gen Psychiatry, vol. 56, 950-951 (1999).
Dursun, S.M. et al., "When treating patients with schizophrenia, what clinical points should be considered if lamotrigine is chosen to augment closapine?," Revue de psychiatrie & de neuroscience, v. 26, No. 2, p. 168 (2001).
Dursun, S.M. et al., "Augmenting antipsychotic treatment with lamotrigine or topiramate in patients with treatment-resistant schizophrenia: a naturalistic case-series outcome study," Journal of Psychopharmacology 15(4), 297-301 (2001).
Eaton, M. et al., "A single intrathecal Injection of GABA permanently reverses neuropathic pain after nerve injury," Brain Research 835, 334-339 (1999).
Emrich, H.M. et al., "Action of Sodium-Valproate and of Oxcarbazepine in Patients with Affective Disorders," Anticonvulsants in Affective Disorders, 45-55 (1984).
Emrich, H.M. et al., "Current Perspectives in the Pharmacopsychiatry of Depression and Mania," Neuropharmacology, vol. 22, No. 3B, 385-388 (1983).
Emrich, H.M. et al., "The Use of Sodium Valproate, Carbamazepine and Oxcarbazepine in Patients with Affective Disorders," Journal of Affective Disorders, 8:243-250 (1985).
Emrich, H.M. et al., "Therapeutic Effects of GABA-ergic Drugs in Affective Disorders. A Preliminary Report," Pharmacology Biochemistry & Behavior, vol. 19, 369-372 (1983).
Emrich, H.M., "Studies with Oxcarbazepine (Trileptal®) in Acute Mania," Int Clin Pharmacol., 5 (Suppl 1), 83-88 (1990).
English language abstract of Cabrera, J. et al., "Kombinierte rezidiv-prophylaktische Behandlung der manisch-depressiven Erkrankung mit Lithium und Carbamazepin oder Oxcarbazepin," Der Nervenarzt, 58:245-249 (1987).
English language abstract of Seidel, M., "Kombinierte rezidiv-prophylaktische Behandlung der manisch-depressiven Erkrangkung mit Lithium und Carbamazepin oder Oxcarbazepin," Der Nervenarzt, 59: 248-249 (1988).
English language Derwent Abstract of EP 0 435 826 A1.
European Agency for the Evaluation of Medicinal Products, "Note for Guidance on Clinical Investigation of Medicinal Products for the Treatment and Prevention of Bipolar Disorder," CPMP/EWP/567/98 (2001).
Farago, F. "Trigeminal Neuralgia: Its Treatment with Two New Carbamazepine Analogues," Eur. Neurol. 26, 73-83 (1987).
Farooque, R., "Uncommon Side Effects Associated with Olanzapine," Pharmacopsychiatry, v. 36, No. 2, 83-86 (2003).
Ficker, D.M. et al., "Improved tolerability and efficacy in epilepsy patients with extended-release carbamazepine," Neurology 65: p. 593-595, August (2 of 2) 2005.
Finnerup, N., "Anticonvulsants in Central Pain," Expert Opin Pharmacother 3(10): 1411-1420, (2002).
Fitzgerald, B. et al., "Elevation of Carbamazepine-10,11-Epoxide by Quetiapine," Pharmacotherapy, vol. 22, No. 11, pp. 1500-1503 (2002).
Freedman, G.M., "Clinical management of common causes of geriatric pain," Geriatrics, 57(5): 36-41 (2002).
French, J.A. et al., "Efficacy and Safety of an extended-release oxcarbazepine (Oxtellar XR™) as adjunctive therapy in patients with refractory partial onset-seizures: a randomized controlled trial," Acta Neurol Scand 2014, 129:143-153.

Friis, M.L. et al., "Therapeutic experiences with 947 epileptic out-patients in oxcarbazepine treatment," ACTA Neurologica Scandinavica, 87(3): p. 224-227 (1993).
Garnett, W.R., "Lamotrigine Interaction with Other Drugs," Antiepileptic Drugs, 5th ed., 380-388 (2002).
Gelder, M. et al., "The International Classification of Diseases (ICD)," Oxford Textbook of Psychiatry, 3rd ed., pp. 67-70 (1996).
Gelenberg, a.J. et al., "Treating Bipolar Disorder: Toward the Third Millennium," Psychiatric Times, vol. XXVII, Issue 4, 3 pages (2001).
Ghose, K et al, "Once daily dosage versus divided daily doses of carbamazepine therapy in epileptic patients: a pilot study" Pharmatherapeutica, 1981, 3(1): 71-78 (abstract only).
Ghose, K. et al., "Effect of Dosage frequency of Carbamazepine: on Drug Serum Levels in Epileptic Patients," Eur J Clin Pharmacol, 1983, 24:375-381.
Gidal, B.E., "Topiramate Drug Interactions," Antiepileptic Drugs, 5th ed., pp. 735-739 (2002).
Gilmer, W. "Anticonvulsants in the treatment of mood disorders: assessing current and future roles," Expert Opin. Pharmacother. 2(10):1597-1608 (2001).
Gloth, F.M. III, "Pain Management in Older Adults: Prevention and Treatment," JAGS 49:188-199 (2001).
Goodnick, P.J. et al., "Use of olanzapine in non-psychotic psychiatric disorders," Exp. Opin. Pharmacother., 2(4): 667-680 (2001).
Grant, S. et al., "Oxcarbazepine: A Review of its Pharmacology and Therapeutic Potential in Epilepsy, Trigeminal Neuralgia and Affective Disorders," Drugs 43(6): 873-888 (1992).
Greil, W. et al., "Prophylactic Treatment of Affective Disorders with Carbamazepine and Oxcarbazepine: An Open Clinical Trial," Psychiatry, The State of the Art, vol. 3, 491-494 (1983).
Haack, K. et al., "The Catalyst Precursor, Catalyst, and Intermediate in the $Ru^{II}$—Promoted Asymmetric Hydrogen Transfer between Alcohols and Ketones," Angew. Chem. Int. Ed. Engl., 36(3): 285-288 (1997).
Hagenah, U. et al., "Tuberöse Sklerose und organische bipolare Störung bei einer 15jährigen Jugendlichen (Tuberous sclerosis and organic bipolar disorder in a 15 year old adolescent)," Z. Kinder-Jugendpsychiatr., 27(4): 283-289 (1999).
Hainzl, D. et al., "Enantioselective Oxidation of 10,11-Dihydro-10-hydroxy-dibenz/b,f/azepine-5-carboxamide, An Active Metabolite of Oxcarbazepine, in the Rat," Br J Pharmacol, 127, 42P.
Harden, R.N., "Complex regional pain syndrome," British Journal of Anaesthesia, 87(1): 99-106 (2001).
Hirschfeld, R.M.A. et al., "A review of the evidence for carbamazepine and oxcarbazepine in the treatment of bipolar disorder," International Journal of Neuropsychopharmacology, 7, 507-522 (2004).
Homs, J.M. et al., "Neuromiotonía congénita. Estudio retrospectivo de cuatro casos," Neurología, 14(7): 328-337 (1999). English Abstract on Title Page.
Hopkins, H.S. et al. "Treating Bipolar Disorder: Toward the Third Millennium," Psych. Times, vol. XVIII, Issue 2, 4 pages. (2001).
Hutt, A.J. et al., "Drug Chirality and its Clinical Significance," Drugs, 52 (Suppl. 5): 1-12 (1996).
Ichikawa, K. et al., "Inhibitory effect of oxcarbazepine on high-frequency firing in peripheral nerve fibers," European Journal of Pharmacology, 420, 119-122 (2001).
International Search Report and Written Opinion for International Application No. PCT/IB2005/002357, dated Dec. 13, 2005.
Janowsky, D.S., "New Treatments of Bipolar Disorder," Curr Psychiatry Rep, 1: 111-113 (1999).
Johannessen, C., "Mechanism of action of valproate: a commentatory," Neurochemistry International, 37, 103-110 (2000).
Karceski, S. et al., "The Expert Consensus Guideline Series: Treatment of Epilepsy," Epilepsy & Behavior 2, A1-A50 (2001).
Keck, P.E., Jr. et al., "A review of randomized, controlled clinical trials in acute mania," Journal of Affective Disorders 59, S31-S37 (2000).
Keck, P.E., Jr. et al., "Anticonvulsants in the Treatment of Bipolar Disorder," Journal of Neuropsychiatry, 4(4): 395-405 (1992).
Keck, P.E., Jr. et al., "Bipolar disorder," Medical Clinics of North America 85(3): 645-61 (2001).

(56) References Cited

OTHER PUBLICATIONS

Khouzam, H.R. et al, "Treatment of Bipolar I Disorder in an Adolescent with Olanzapine," Journal of Child Adolescent Psychopharmacology, 10(2): 147-151 (2000).
Kiguchi, S. et al., "Suppressive Effects of Oxcarbazepine on Tooth Pulp-Evoked Potentials Recorded at the Trigeminal Spinal Tract Nucleus in Cats," Clinical and Experimental Pharmacology and Physiology, 28: 169-175 (2002).
Krämer, G. "Oxcarbazepine—Adverse Effects," Antiepileptic Drugs, 5th Ed., pp. 479-486 (2002).
Learmonth, D. et al. "Synthesis, anticonvulsant properties and pharmacokinetic profile of novel 10,11-dihydro-10-oxo-5H-dibenz/b,f/azepine-5-carboxamide derivatives," Eur J Med Chem 36: 227-236 (2001).
Lemke, M.R., "Effect of Carbamazepine on Agitation in Alzheimer's Inpatients Refractory to Neuroleptics," J Clin Psychiatry 56(8): 354-357 (1995).
Leppik, I.E., "Antiepileptic Drugs in Development: Prospects for the Near Future," Epilepsia, 35 (Suppl. 4): S29-S40 (1994).
Lessig, M.G. et al., "Topirimate for Reversing Atypical Antipsychotic Weight Gain," J Am Acad Child Adolesc Psychiatry, 40(12): 1364 (2001).
Levy, E. et al., "Topiramate Produced Weight Loss Following Olanzapine-Induced Weight Gain in Schizophrenia," J Clin Psychiatry, 63(11): 1045 (2002).
Levy, R.H. et al., *Antiepileptic Drugs*, $5^{th}$ Edition, Lippincott Williams & Wilkins, PA (2002).
Levy, G., "A Pharmacokinetic perspective on medicament noncompliance," Clinical Pharmacology & Therapeutics, vol. 54, No. 3, p. 242-244 (Sep. 1993).
Lisgarten, J.N. et al., "The Structure of 10,11-Dihydro-10-hydroxy-5H-dibenz[b,f]azepine-5-carboxamide, an Anticonvulsant Drug Molecule," Acta Cryst, C45: 656-658 (1989).
Lloyd, P. et al., "Clinical Pharmacology and Pharmacokinetics of Oxcarbazepine," Epilepsia, 35 (Suppl. 3): S10-S13 (1994).
Löscher, W., "Valproate: A Reappraisal of its Pharmacodynamic Properties and Mechanisms of Action," Progress in Neurobiology, vol. 58, pp. 31-59 (1999).
Maia, J. et al., "Effect of Eslicarbazepine Acetate (BIA 2-093) on the Steady State Pharmacokinetics of Digoxin in Healthy Subjects," Epilepsia, 46(Suppl 6): p. 283 (2005).
Maia, J. et al., "BIA 2-093 as add-on therapy for refractory partial epilepsy in adults," Epilepsia, vol. 45(Suppl 3), p. 158, abstract p. 410 (2004).
Maia, J. et al., "Effect of Eslicarbazepine Acetate (BIA 2-093) on the Steady-state Pharmacokinetics of Digoxin in Healthy Subjects," poster at 26th International Epilepsy congress, *Epilepsia*, vol. 46(Suppl 6), p. 283 (2005).
Maia, J. et al., "Effect of Food on the Pharmacokinetic Profile of Eslicarbazepine Acetate (BIA 2-093)," Drugs R D, 6(4): 201-206 (2005).
Margineanu, D.G. et al., "UCB 34714, a new pyrrolidone anticonvulsant, had no effect on voltage-gated potassium currents in cultured mouse hippocampal neurons," Abstracts from the 6th European Congress on Epileptology, Journal of the International LeagueAgainst Epilepsy, Epilepsia, vol. 45, Suppl. 3, p. 116 (2004).
Marmarou, A. et al., "Zonisamide: Physician and patient experiences," Epilepsy Research, 64, p. 63-69 (2005).
May, T.W. et al., "Fluctuations of 10-hydroxy-carbazepine during the day in epileptic patients," Acta Neurol Scand 93: 393-397 (1996).
McElroy, S.L. et al., "Pharmacologic Agents for the Treatment of Acute Bipolar Mania," Society of Biological Psychiatry, 48: 539-557 (2000).
McKee, PJW. et al, "Double dummy comparison between once and twice daily dosing with modified-release carbazepine in epileptic patients," Br J Clin Pharmac, 1993, 36: 257-261.
McLean, M.J., "Oxcarbazepine—Mechanisms of Action," Antiepileptic Drugs, 5th Ed., pp. 451-458 (2002).
Meldrum, B. "Pharmacology of GABA," Clinical Neuropharmacology vol. 5, No. 3, pp. 293-316 (1982).
Meyerson, B.A. et al., "Modulation of Spinal Pain Mechanisms by Spinal Cord Stimulation and the Potential Role of Adjuvant Pharmacotherapy," Stereotact Funct Neurosurg, 68: 129-140 (1997).
Mohar, B. et al., "Highly enantioselective synthesis via dynamic kinetic resolution under transfer hydrogenation using Ru(η6-arene)-N-perfluorosulfony1-1,2-diamine catalysts: a first insight into the relationship of the ligand's pKa and the catalyst activity," Chem. Commun, pp. 2572-2573 (2001).
Müller, A.A. et al., "Carbamazepine and Oxacarbazepine in the Treatment of Manic Syndromes—Studies in Germany," Anticonvulsants in Affective Disorders, pp. 139-147 (1984).
Müller, A.A, et al., "Oxcarbazepine in Acute Mania," Psychiatry, The State of the Art, vol. 3, pp. 495-500 (1983).
Navarro, V. et al., "Topiramate for Clozapine-Induced Seizures," Am J Psychiatry, 158(6): 968-969, 2001.
Nunes, T. et al., "Eslicarbazepine acetate (BIA 2-093): Relative bioavailability and bioequivalence of 50 mg/mL oral suspension and 200 mg and 800 mg tablet formulations," poster at 26th Internet' Drugs R & D, 6 (5) 253-260 (2005).
Fontes-Ribeiro, C. et al., "Eslicarbazepine acetate (BIA 2-093): Relative bioavailability and bioequivalence of 50 mg/mL oral suspension and 200 mg and 800 mg tablet formulations," Drugs R & D, 6 (5) 253-260 (2005).
Parada, A. et al., "The novel anticonvulsant BIA 2-093 inhibits transmitter release during opening of voltage-gated sodium channels: a comparison with carbamazepine and oxcarbazepine," Neurochemistry International, 40: 435-440 (2002).
Patsalos, Philip N., et al., "Clinically Important drug interactions in epilepsy: general features and interactions between antiepileptic drugs", The Lancet Neurology, Jun. 2003, pp. 347-356, vol. 2.
Pavuluri, M. et al., "Topiramate Plus Risperidone for Controlling Weight Gain and Symptoms in Preschool Mania," Journal of Child and Adolescent Psychopharmacology, vol. 12, No. 3, 271-273 (2002).
Pellock, J.M. et al., "Extended-Release Formulations: Simplifying Strategies in the Management of Antiepileptic Drug Therapy," Epilepsy & Behavior, 5 (2004), p. 301-307.
Petty, F. "GABA and mood disorders: a brief review and hypothesis," J Affective Disorders 34: 275-281 (1995).
Petty, F. et al., "Low Plasma GABA Is a Trait-Like Marker for Bipolar Illness," Neurophyschopharmacology, vol. 9, No. 2, pp. 125-132 (1993).
Pisani, F. et al., "Lamotrigine—Adverse Effects," Antiepileptic Drugs, 5th ed., pp. 408-416 (2002).
Post, R.M. et al., "The place of anticonvulsant therapy in bipolar illness," Psychopharmacology 128: 115-129 (1996).
Price, P.L. "Olanzapine to treat the acute mania of bipolar disorder," S D J Med, 53: 523 (2000).
Reinikainen, K.J. et al., "Comparison of Oxcarbazepine and Carbamazepine: A Double-Blind Study," Epilepsy Res., 1 (1987), p. 284-289.
Rogvi-Hansen et al, "Adverse Effects of Established and New Antiepileptic Drugs: An Attempted Comparison," Pharmac. Ther. (1995) 68(3): 425-434.
Rosenberg, J. et al., "The Effect of Gabapentin on Neurophathic Pain," The Clinical Journal of Pain, 13: 251-255 (1997).
Rosner, H. et al., "Gabapentin Adjunctive Therapy in Neuropathic Pain States," The Clinical Journal of Pain, 12: 56-58 (1996).
Rowbotham, M.et al., "Gabapentin for the Treatment of Postherpectic Neuralgia," JAMA, vol. 280, No. 21, pp. 1837-1842 (1994).
Saba, G. et al., "Lamotrigine—Clozapine Combination in Refractory Schizophrenia: Three Cases," J. Neuropsychiatry Clin Neurosc 14(1): 86 (2002).
Sadock, B. et al., "Epidemiology—Incidence and Prevalence," Synopsis of Psychiatry—Behavioral Sciences/Clinical Psychiatry, 9th ed., pp. 535.
Sander, "The Use of Antiepileptic Drugs—Principles and Practice," Epilepsia 45(Supp 6): 28-34 (2004).

(56) References Cited

OTHER PUBLICATIONS

Schachter, S.C. et al., "Oxcarbazepine, Double-Blind, Randomized, Placebo-Controled, Monotherapy Trial for Partial Seizures," Neurology, 52: p. 732-737, Mar. (1 of 2) 1999.
Scheyer, R.D., "Valproic Acid—Drug Interactions," Antiepileptic Drugs, 5th ed., pp. 801-807 (2002).
Schmitz, B. et al, "Introduction," Epilepsia, vol. 46 (Suppl. 4): 1-2 (2005).
Schmutz, M. et al., "Oxcarbazepine: Preclinical Anticonvulsant Profile and Putative Mechanisms of Action," Epilepsia, vol. 35 (Suppl. 5): S47-S50 (1994).
Schütz, H. et al., "The metabolism of 14C-oxcarbazepine in man," Xenobiotica, vol. 16(8): 769-778 (1986).
Seidel, M., "Kombinierte rezidiv-prophylaktische Behandlung der manisch-depressiven Erkrangkung mit Lithium and Carbamazepin oder Oxcarbazepin," Der Nervenarzt, 59: 248-249 (1988). English.
Sharief, M., "Double-blind, placebo-controlled study of topiramate in patients with refractory partial epilepsy", Epilepsy Research 25 (1996) 217-224.
Shua-Haim, J., "Oxcarbazepine in the management of behavioral agitation in community-dwelling patients with Alzheimer's disease: An open-label study," S434, P.6.019.
Sierra-Paredes, G. et al., "Effect of novel anticonvulsant BIA 2-093 on seizures induced by picrotoxin microperfusion in the rat hippocampus," Abstracts from the 6th European Congress on Epileptology, Journal of the International League Against Epilepsy,Epilepsia, vol. 45, Suppl. 3, pp. 116, p. 243, 2004.
Silveira, P. et al. "BIA 2-093 pharmacokinetics in healthy elderly subjects," Epilespsia, 45 (Supple. 3), 157 p. 409 (2004).
Simanski, C., et al., "Akutschmerztherapie und-management in der Orthopädie," Der Orthopäde, vol. 31: 522-533 (2002).
Simanski, C. et al., "Acute Pain Therapy and Management in Orthopedics," Der Orthopäde, vol. 31: 522-533 (2002). (English Translation).
Stefan, H. et al., "Clinical Monitoring During Carbamazepine Slow-Release, Once-Daily Monotherapy," Epilepsia, vol. 29, No. 5, p. 571-577, 1988.
Stiller, C. et al., "Release of γ-Aminobutyric Acid in the Dorsal Horn and Suppression of Tactile Allodynia by Spinal Cord Stimulation in Mononeuropathic Rats," Neurosurgery, vol. 39(2): 367-375 (1996).
Stubley, L. et al, "Only Early Intervention with Gama-Aminobutyric Acid Cell Therapy Is Able to Reverse Neuropathic Pain After Partial Nerve Injury," J. Neurotrauma, vol. 18(4): 471-477 (2001).
Świąder, M. et al., "Influence of LY 300164, An AMPA/Kainate Receptor Antagonist Upon the Anticonvulsant Action of Antiepileptic Drugs Against Aminophylline-Induced Seizures in Mice," Pol J Pharmacol, 55: 103-107 (2003).
Taran, F. et al. "High-Throughput Screening of Enantioselective Catalysts by Immunoassay," Angew. Chem. Int. Ed., 41(1): 124-127 (2002).
Tegretol Prescribing Information, T2000-04, 89007002, Rev. Feb. 2000.
Teitelbaum, M., "Oxcarbazepine in BipolarDisorder," J Am Acad Child Adolescent Psychiatry, 40(9): 993-994 (2001).
Tohen, M. et al. "Efficacy of Olanzapine in Acute Bipolar Mania: A Double-blind, Placebo-controlled Study," Arch Gen Psychiatry, 57: 841-849 (2000).
Tohen, M. et al. "Onset of action of antipsychotics in the treatment of mania," Bipolar Disord, 2: 261-268 (2000).
Trileptal Prescribing Information, T2005, NDA 21-014/SLR-012, NDA 21-285/SLR-007.
Trimble, M., "Oxcarbazepine—Clinical Efficacy and Use in Psychiatric Disorders," Antiepileptic Drugs, 5th Ed., pp. 476-478 (2002).
Urquhart, J., "Ascertaining How Much Compliance is Enough with Outpatient Antibiotic Regimens," Postgrad Med. J. (1992) 68 (Suppl. 3), p. S49-S59.
Van Parys, J.A.P. et al., "Survey of 260 Epileptic Patients Treated with Oxcarbazepine (Trileptal®) on a Named-Patient Basis," Epilepsy Research 19 (1994) p. 79-85.
Vartiainen, H. et al., "Carbamazepine and Oxcarbazepine in the Treatment of Aggression," Psychopharmacology, vol. 114(3): B13, abstract 44 (1994).
Vaz-Da-Silva et al., "Eslicarbazepine Acetate Pharmacokinetics after Single and Repeated Doses in Healthy Subjects," Epilepsia (2005) 46(Supp 8): 191 (2005).
Vaz-da-Silva, M. et a., "Influence of food on the pharmacokinetics of the antiepileptic agent BIA 2-093."
Velikonja, M. et al, "Effect of Oxcarbazepine (CG 47.680) on Affective and Schizoaffective Symptoms—A Preliminary Report," Anticonvulsants in Affective Disorders, pp. 208-210 (1984).
Vicenzini et al., "Clinical and neuropsychological effects of Carbamazepine, Oxcarbazepine, and Levetiracetam in healthy volunteers," Boll Lega It Epil, 2002, No. 118, 173-175.
Vieta, E. et al. "Olanzapine as Long-Term Adjunctive Therapy in Treatment-Resistant Bipolar Disorder," J Clin Psychopharmacol, 21: 469-473 (2001).
Volosov, A. et al., "Comparative Stereoselective Pharmacokinetic Analysis of 10-Hydroxycarbazepine After Oral Administration of its Individual Enantiomers and the Racemic Mixture to Dogs," Epilepsia, vol. 41(9): 1107-1111 (2000).
Volosov, A. et al., "Stereoselective Pharmacokinetic Analysis of the Antiepileptic 10-Hydroxycarbazepine in Dogs," Therapeutic Drug Monitoring, 21: 219-223 (1999).
Von Unruh, G.E. et al., "Gas Chromatographic Assay for Oxcarbazepine and its Main Metabolites in Plasma," Journal of Chromatography Biomedical Applications, vol. 345(1): 67-76 (1985).
Walden, J. et al., "Bedeutung alter and neuer Antiepileptika in der Behandlung psychischer Erkrankungen (Significance of Old and New Antiepileptic Drugs in the Treatment of Psychiatric Diseases)," Fortschr Neurol Psychiat, 63: 320-335 (1995).
Wang, P. W. et al., "Gabapentin augmentation therapy in bipolar depression," Bipolar Disorders, 4: 296-301 (2002).
Weber, W.E.J., "Farmacotherapie van neuropathische pijn door letsel van afferente zenuwvezels," Ned Tijdschr Geneeskd 145(17): 813-817 (2001).
Weber, W.E.J., "Pharmacotherapy of neuropathic pain caused by damage to afferent nerve fibres", Ned Tijdschr Geneeskd 2001, Apr. 28, 2001, 145 (17), 1-5. (English translation).
Weisler, RH et al., "Efficacy and Safety of Once—versus Twice-Daily Carbazepine Extended-Release Capsules for the Treatment of Manic Symptoms in Patients with Bipolar I Disorder," Psychiatry (Edgmont), 2008, 5(3): 35-48.
Wildgrube, C. "Case Studies on Prophylactic Long-term Effects of Oxcarbazepine in Recurrent Affective Disorders," Inter Clin Psychopharmacol, 5(Suppl. 1): 89-94 (1990).
Zakrzewska, J.M. et al. "Oxcarbazepine: a new drug in the management of intractable trigeminal neuralgia," Journal of Neurology, Neurosurgery, and Psychiatry, 52: 472-476 (1989).
Zarnowski, T. et al., "NBQX—A Selective AMPA Antagonist Enhances Antiepileptic Properties of Common Anticonvulsant Drugs Against Maximal Electroshock in Mice," Polish J Pharmacology & Pharmacy, vol. 44: 258-259 (1992).
Oxford Dictionary of Biochemistry and Molecular Biology, 1997, Oxford University Press, p. 288.
The Handbook of Clinical Trials and Other Research, 2002, Radcliffe Medical Press Ltd, pp. 247-251.
Nunes, T. et al., "Steady-state plasma and cerebrospinal fluid pharmacokinetics and tolerability of eslicarbazepine acetate and oxcarbazepine in healthy volunteers," Epilepsia, 2013, 54(1): 108-116.
Rowland and Tozer, "Clinical Pharmacokinetics, Concepts and Applications," 1995, Lippincott Williams & Wilkins, 3rd. Ed., pp. 89-90.

US 9,763,954 B2

THERAPEUTICAL USES OF ESLICARBAZEPINE

CROSS-REFERENCE TO RELATED APPLICATIONS

This application is a continuation application U.S. application Ser. No. 12/522,535 filed on Sep. 18, 2009, which is a national stage filing unde 35 U.S.C. §317 of International Application No. PCT/PT2008/000002 filed on Jan. 14, 2008, which claims priority of United Kingdom Patent Application No. 0700773.5, filed Jan. 15, 2007. The contents of these applications are incorporated herein by reference.

FIELD OF THE INVENTION

This invention relates to drug therapies. More particularly the invention relates to the therapeutical use of eslicarbazepine and eslicarbazepine acetate.

As used in the specification the term "eslicarbazepine acetate" means (S)-(−)-10-acetoxy-10,11-dihydro-5H-dibenz/b,f/azepine-5-carboxamide. Also as used in this specification the term eslicarbazepine or S-licarbazepine means (S)-(+)-10,11-dihydro-10-hydroxy-5H dibenz/b,f/ azepine-5-carboxamide.

BACKGROUND OF THE INVENTION

Eslicarbazepine acetate, (S)-(−)-10-acetoxy-10,11-dihydro-5H-dibenz/b,f/azepine-5-carboxamide, is a new drug currently being developed which is useful for the treatment of various conditions, such as, for example, epilepsy and affective brain disorders, as well as pain conditions and nervous function alterations in degenerative and post-ischemic diseases. Although chemically related to carbamazepine and oxcarbazepine, eslicarbazepine acetate is believed to avoid the production of certain toxic metabolites (such as, for example, epoxides) and to avoid the unnecessary production of enantiomers or diastereoisomers of metabolites and conjugates, without losing pharmacological activity (Almeida et al., 2005a; Almeida et al., 2005b; Almeida et al., 2002; Almeida et al., 2003; Almeida et al., 2004; Benes et al., 1999; Bialer et al., 2004; Soares-da-Silva, 2004). Unlike oxcarbazepine, eslicarbazepine acetate is almost entirely metabolized to the active metabolite eslicarbazepine (Almeida et al., 2005a; Almeida et al., 2005b).

Throughout the specification, the term "pharmacoresistant", and variations thereon, will be understood to relate to a condition where the patient is not responsive to pharmaceutical treatment at all;

the term "refractory" will be understood to relate to a condition wherein the patient becomes progressively less responsive to their medication and, in the case of epilepsy, suffers from an increasing number of seizures; and the term "intractable", and variations thereon, will be understood to signify difficult-to-treat or treatment(drug)-resistant and thus encompasses both pharmacoresistant and refractory conditions.

Resistance to pharmacological therapy (pharmacoresistance) is one of the major problems in the treatment of epilepsy (Löscher et al., 2004). Approximately one third of all epilepsy patients do not become seizure free, despite treatment with two or more antiepileptic drugs (AEDs) at a maximal tolerated dose. This intractability is even higher (50-70%) in patients with temporal lobe epilepsy (Kwan et al., 2000; Mohanraj et al., 2005; Schmidt et al., 2005; Stephen et al., 2006). Although the causes and mechanisms underlying pharmacoresistance are not fully understood, drug-efflux transporters of the adenosine triphosphate (ATP)-binding cassette (ABC) family (multidrug transporters) may play an important role. P-glycoprotein (P-gp or ABCB1 or MDR1) is the most extensively studied multidrug transporter. In fact, P-gp transports a variety of xenobiotics, including commonly used AEDs (Potschka et al., 2002; Potschka et al., 2001a; Potschka et al., 2001b; Rizzi et al., 2002; Sills et al., 2002).

In fact, a current popular hypothesis is that overexpression of drug efflux ("multidrug") transporters at the brain capillary endothelium induced by repetitive seizure activities lowers AED concentration in brain interstitial fluid and contributes to drug resistance (Kwan et al., 2005; Löscher et al., 2005a; Löscher et al., 2005b; Schmidt et al., 2005). Several studies have shown that such drug efflux transporters, including P-glycoprotein (P-gp or MDR1) and members of the multidrug resistance protein (MRP) family, are overexpressed in surgically resected brain tissue from patients with medically intractable epilepsy (Kwan et al., 2005; Löscher et al., 2005a; Löscher et al., 2005b; Schmidt et al., 2005). Furthermore, in epileptogenic brain tissue from patients with pharmacoresistant epilepsy, an overexpression of several multidrug transporters, including P-glycoprotein (P-gp) and members of the multidrug resistance protein (MRP) family such as MRP1 and MRP2 has been reported (Aronica et al., 2003; Dombrowski et al., 2001; Sisodiya et al., 2002; Tishler et al., 1995). Overexpression was found both in brain capillary endothelial cells that form the blood—brain barrier (BBB) and in astrocytes and astrocyte processes that ensheath the endothelial cells and contribute to BBB function. In human refractory epileptic brain tissue (Aronica et al., 2003; Aronica et al., 2004; Marchi et al., 2004; Sisodiya et al., 2002; Tishler et al., 1995), as well as in the epileptic rat brain (van Vliet et al., 2004; Volk et al., 2004a; Volk et al., 2004b), P-gp is overexpressed in endothelial cells, neurons, and glial cells. P-gp overexpression, particularly in endothelial cells, may lead to increased extrusion of drugs from the brain to the blood, preventing the attainment of appropriate AED concentrations at therapeutic targets. Because multidrug transporters such as P-gp and MRPs accept a wide range of drugs as substrates, overexpression of such efflux transporters in the BBB would be one likely explanation for resistance to various AEDs in a patient with intractable epilepsy (Kwan et al., 2005; Löscher et al., 2005a; Löscher et al., 2005b; Schmidt et al., 2005).

The consequences of uncontrolled epilepsy can be severe, and include shortened lifespan, bodily injury, neuropsychological and psychiatric impairment, and social disability (Sperling, 2004). Most patients with refractory epilepsy are resistant to several, if not all, AEDs, despite the fact that these drugs act by different mechanisms (Kwan et al., 2000; Sisodiya, 2003). This multidrug type of resistance argues against epilepsy-induced alterations in specific drug targets as the main cause of pharmacoresistant epilepsy, pointing instead to nonspecific and possibly adaptive mechanisms (Sisodiya, 2003). Epilepsy was the first CNS disorder for which drug resistance was associated with enhanced expression of multidrug transporters in the brain (Tishler et al., 1995). The expression of multidrug transporters in the astroglial end-feet covering the blood vessels that are found in epileptogenic brain tissue might represent a 'second barrier' under these conditions (Abbott, 2002; Sisodiya et al., 2002). Several widely used AEDs, which have been made lipophilic to allow them to penetrate the brain, are substrates for P-gp or MRPs in the BBB (Potschka et al., 2002; Potschka et al., 2001a; Potschka et al., 2003; Potschka et al., 2001b; Rizzi et al., 2002; Schinkel et al., 1996; Sills et al., 2002; Tishler et al., 1995). As a result, the uptake of these drugs by the brain can be increased by knocking out or blocking P-gp. The overexpression of these transporters in epileptogenic tissue is likely, therefore, to reduce the amount of drug that reaches the epileptic neurons. This is one plausible explanation for multidrug resistance in epilepsy (Sisodiya, 2003).

Although the multidrug transporter hypothesis of intractable epilepsy is biologically plausible, it has not been proven (Löscher et al., 2004; Sisodiya, 2003). Despite the fact that high P-gp expression has been shown in epileptogenic brain tissue from patients with intractable epilepsy, adequate controls are lacking, as it is impossible to compare this tissue directly with tissue from patients who respond well to AED treatment (because these patients do not need to undergo surgical resection of epileptogenic foci). Consequently, it is not clear whether the increased P-gp expression in patients with drug-resistant epilepsy is a cause of pharmacoresistance or just a result of uncontrolled seizures—or an epiphenomenon that occurs in epileptic brain tissue irrespective of drug response. For direct proof-of-principle, it should be established whether P-gp inhibitors counteract multidrug resistance in epilepsy. In line with this suggestion, Summers et al. (Summers et al., 2004) recently reported that combined treatment with verapamil and AEDs greatly improved overall seizure control and subjective quality of life in a patient with intractable epilepsy. Verapamil is a calcium channel blocker that is transported by P-gp and competitively blocks the transport of other substrates by P-gp (Schinkel et al., 2003). Because of its efficient efflux transport by P-gp at the BBB, verapamil itself does not penetrate into the brain (Kortekaas et al., 2005), so the improved seizure control observed both experimentally and clinically in response to co-administration of verapamil and AEDs is not secondary to the calcium channel-blocking effect of verapamil. Following the promising clinical results of combined treatment with verapamil and AEDs (Summers et al., 2004), Summers et al. went on to test combinations of AEDs and verapamil in other patients with drug-resistant epilepsy, again with a favourable outcome (for details see (Löscher et al., 2005a)).

Oxcarbazepine has been used either in monotherapy or in adjunctive therapy in patients with partial-onset seizures with or without secondary generalization (May et al., 2003; Schmidt et al., 2001; Shorvon, 2000; Tartara et al., 1993). Oxcarbazepine undergoes rapid 10-keto reduction to a mixture of S-licarbazepine and R-licarbazepine the racemic mixture if which is usually referred as licarbazepine (10-hydroxy-10,11-dihydrocarbazepine, 10-OHCBZ, or MHD) (Faigle et al., 1990; Feldmann et al., 1978; Feldmann et al., 1981; Flesch et al., 1992; Schutz et al., 1986; Volosov et al., 1999).

Recently, licarbazepine (10-OHCBZ) was suggested not to cross the blood-brain barrier by simple diffusion, namely being a substrate of P-gp. In fact, the level of expression of MDR1 was found to be inversely correlated with 10-OHCBZ concentration in the epileptic tissue (Marchi et al., 2005). It was concluded that P-gp may play a role in the resistance to oxcarbazepine by determining the attainment of insufficient concentrations of its active metabolite at neuronal targets (Marchi et al., 2005). In the rat, which does not convert oxcarbazepine to licarbazepine (10-OHCBZ), co-administration of the P-gp inhibitor verapamil significantly potentiated the anticonvulsant activity of oxcarbazepine in the pilocarpine seizure model (Clinckers et al., 2005). However, it remains to be determined whether P-gp or MRPs are endowed with identical affinity for S-licarbazepine and R-licarbazepine.

SUMMARY OF THE INVENTION

We have now unexpectedly discovered that S-licarbazepine is not a substrate for P-glycoprotein (P-gp) or Multiple Resistant Proteins (MRPs). This discovery offers opportunities for the treatment of pharmacoresistant epilepsy, and other conditions.

We have also unexpectedly discovered an enhanced brain exposure to S-licarbazepine versus that conferred by R-licarbazepine. The enhanced brain penetration of S-licarbazepine correlated positively with the enhanced efficacy of S-licarbazepine versus R-licarbazepine in experimental models of epileptogenesis (corneal kindling) and pain.

We have also unexpectedly discovered that inhibitors of P-gp or MRPs do not interfere with the brain penetration of the main active metabolite of eslicarbazepine acetate, S-licarbazepine, a discovery that offers opportunities for the treatment of pharmacoresistant epilepsy with eslicarbazepine acetate.

Due to the unexpected potential of eslicarbazepine, the main active metabolite of eslicarbazepine acetate, to not serve as a substrate for efflux pumps such as P-gp and MRP, and therefore not require adjunctive administration of a P-gp or MRP inhibitor these compounds are considered to offer advantages over other AEDs for the clinical management of difficult-to-treat patients afflicted with epilepsy, central and peripheric nervous system disorders, affective disorders, schizoaffective disorders, bipolar disorders, attention disorders, anxiety disorders, neuropathic pain and neuropathic pain-related disorders, sensorimotor disorders, vestibular disorders, and nervous function alterations in degenerative and post-ischemic diseases.

BRIEF DESCRIPTION OF THE DRAWINGS

Reference is made to the accompanying drawings, in which.

DETAILED DESCRIPTION

Figure 1:
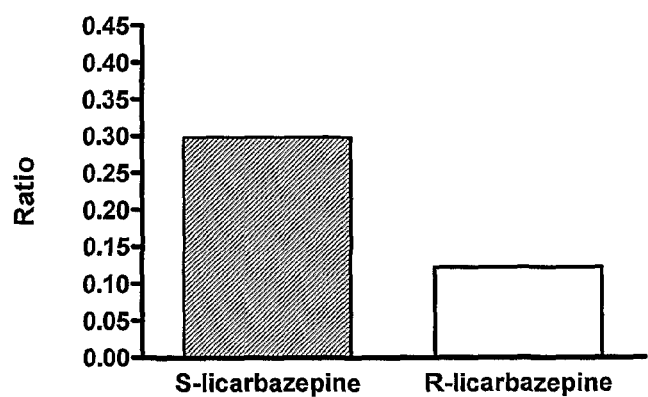
FIG. 1 is a graph showing the brain/plasma ratio (Cmax and AUC) for S-licarbazepine and R-licarbazepine.
Figure 1:
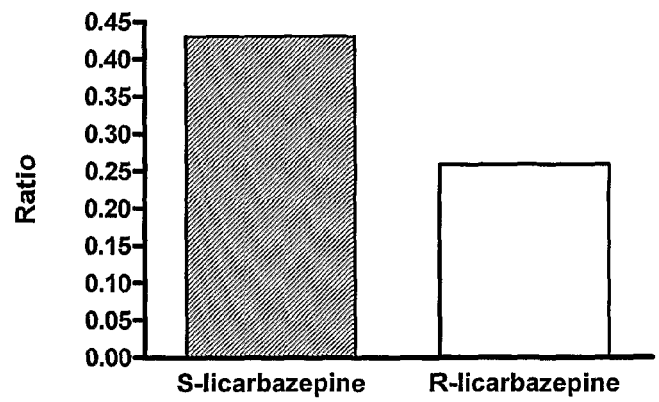

According to one aspect of the invention there is provided the use of eslicarbazepine or eslicarbazepine acetate in the manufacture of a medicament for treating a condition selected from epilepsy, central and peripheral nervous system disorders, affective disorders, schizoaffective disorders, bipolar disorders, attention disorders, anxiety disorders, neuropathic pain and neuropathic pain-related disorders, sensorimotor disorders, vestibular disorders, and nervous function alterations in degenerative and post-ischemic diseases in circumstances where the use of a P-glycoprotein inhibitor or a Multiple Resistant Protein inhibitor would adversely affect the subject being treated.

For example, the administration of the P-glycoprotein inhibitor, verapamil, adversely affects subjects suffering from a heart condition. Thus, the administration of eslicarbazepine or eslicarbazepine acetate to a patient suffering from a heart condition, and who is also suffering from one or more of said selected conditions mentioned above, enables the selected condition or conditions to be treated effectively without the need for administering a P-glycoprotein inhibitor or a Multiple Resistant Protein inhibitor.

Examples of heart conditions which are adversely affected by the administration of verapamil include: Bradycardia; second and third degree atrioventricular block; heart failure; Wolff-Parkinson-White syndrome; patients using beta-blocker treatment.

Contra-indications for cyclosporine include but are not limited to: patients hypersensitive to cyclosporine, uncontrolled hypertension, premalignant skin lesions or current malignancies, chickenpox and herpes zoster, renal or hepatic impairment, patients suffering from any type of bacterial or viral infection.

Contra-indications for probenecid include but are not limited to: hypersensitivity to probenecid or colchicine, patients under 2 years of age, blood dyscrasias, uric acid kidney stones.

Thus, the administration of eslicarbazepine or eslicarbazepine acetate to a patient suffering from one of the contra-indicated conditions or falling into one of the contra-indicated categories listed above, and who is also suffering from one or more of epilepsy, central and peripheral nervous system disorders, affective disorders, schizoaffective disorders, bipolar disorders, attention disorders, anxiety disorders, neuropathic pain and neuropathic pain-related disorders, sensorimotor disorders, vestibular disorders, and nervous function alterations in degenerative and post-ischemic diseases, enables this latter condition or conditions to be treated effectively without the need for administering a P-glycoprotein inhibitor or a Multiple Resistant Protein inhibitor.

According to a further aspect of the invention there is provided the use of eslicarbazepine acetate or eslicarbazepine in the manufacture of a medicament for treating a drug resistant condition selected from epilepsy, central and peripheral nervous system disorders, affective disorders, schizoaffective disorders, bipolar disorders, attention disorders, anxiety disorders, neuropathic pain and neuropathic pain-related disorders, sensorimotor disorders, vestibular disorders, and nervous function alterations in degenerative and post-ischemic diseases, wherein the patient to be treated is suffering from a condition which requires administration of a drug which reacts adversely with a P-gp inhibitor or an MRP inhibitor.

Examples of P-glycoprotein inhibitors and Multiple Resistant Protein inhibitors include: cyclosporin, verapamil, valspodar, biricodar, probenecid, elacridar, tariquidar XR9576, zosuquidar LY335979, laniquidar R101933, ONT-093.

According to another aspect of the invention there is provided the use of eslicarbazepine or eslicarbazepine acetate in the manufacture of a medicament for treating an intractable condition selected from epilepsy, central and peripheral nervous system disorders, affective disorders, schizoaffective disorders, bipolar disorders, attention disorders, anxiety disorders, neuropathic pain and neuropathic pain-related disorders, sensorimotor disorders, vestibular disorders, and nervous function alterations in degenerative and post-ischemic diseases.

Preferably the intractable condition is, at least in part, caused by an overexpression of P-gp or MRP.

Preferably the intractable state of the condition is, at least in part, due to an overexpression of P-gp or MRP.

Preferably the intractable condition is a pharmacoresistant condition.

In an alternative embodiment, the intractable state of the condition is due to the patient's being resistant to treatment with a pharmaceutical which is not a substrate for P-gp or MRP.

Preferably the intractable condition is a pharmacoresistant condition.

In the above aspects of the invention, preferably the eslicarbazepine or eslicarbazepine acetate is administered as a monotherapy for treating said condition. Preferably the eslicarbazepine or eslicarbazepine acetate is administered in the absence of a P-glycoprotein inhibitor, such as verapamil, or a Multiple Resistant Protein inhibitor, such as probenecid.

According to another aspect of the invention there is provided the use of eslicarbazepine or eslicarbazepine acetate, in combination with a second drug which reacts adversely with a P-glycoprotein inhibitor or a Multiple Resistant Protein inhibitor, in the manufacture of a medicament for treating a condition selected from epilepsy, central and peripheral nervous system disorders, affective disorders, schizoaffective disorders, bipolar disorders, attention disorders, anxiety disorders, neuropathic pain and neuropathic pain-related disorders, sensorimotor disorders, vestibular disorders, and nervous function alterations in degenerative and post-ischemic diseases.

The second drug may be a drug for the treatment of bradycardia; second and third degree atrioventricular block; heart failure; or Wolff-Parkinson-White syndrome; uncontrolled hypertension; premalignant skin lesions or current malignancies; chickenpox or herpes zoster; renal or hepatic impairment; any type of bacterial or viral infection; blood dyscrasias; or uric acid kidney stones.

The condition may be an intractable condition.

Preferably the intractable condition is, at least in part, caused by an overexpression of P-gp or MRP.

Preferably the intractable state of the condition is, at least in part, due to an overexpression of P-gp or MRP.

Preferably the intractable condition is a pharmacoresistant condition.

Preferably the intractable condition is a refractory condition.

In an alternative embodiment, the intractable state of the condition is due to the patient's being resistant to treatment with a pharmaceutical which is not a substrate for P-gp or MRP.

Preferably the intractable condition is a pharmacoresistant condition.

Preferably the intractable condition is a refractory condition.

Preferably the eslicarbazepine or eslicarbazepine acetate and the second drug are administered in the absence of a P-glycoprotein inhibitor, such as verapamil, or a Multiple Resistant Protein inhibitor, such as probenecid.

According to another aspect of the invention there is provided the use of eslicarbazepine or eslicarbazepine acetate, in combination with a drug to treat a heart condition, in the manufacture of a medicament for treating said heart condition and a further condition selected from epilepsy, central and peripheral nervous system disorders, affective disorders, schizoaffective disorders, bipolar disorders, attention disorders, anxiety disorders, neuropathic pain and neuropathic pain-related disorders, sensorimotor disorders, vestibular disorders, and nervous function alterations in degenerative and post-ischemic diseases.

The drug for treating the heart conditions may be a drug for the treatment of bradycardia; second and third degree atrioventricular block; heart failure; or Wolff-Parkinson-White syndrome.

According to another aspect of the invention there is provided the use of eslicarbazepine or eslicarbazepine acetate, in combination with a drug to treat one or more of the following conditions: uncontrolled hypertension, premalignant skin lesions or current malignancies, chickenpox and herpes zoster, renal or hepatic impairment, any type of bacterial/viral infection, blood dyscrasias, and uric acid kidney stones, in the manufacture of a medicament for treating said condition and a further condition selected from epilepsy, central and peripheric nervous system disorders, affective disorders, schizoaffective disorders, bipolar disorders, attention disorders, anxiety disorders, neuropathic pain and neuropathic pain-related disorders, sensorimotor disorders, vestibular disorders, and nervous function alterations in degenerative and post-ischemic diseases.

The epilepsy, central and peripheric nervous system disorders, affective disorders, schizoaffective disorders, bipolar disorders, attention disorders, anxiety disorders, neuropathic pain and neuropathic pain-related disorders, sensorimotor disorders, vestibular disorders, and nervous function alterations in degenerative and post-ischemic diseases may be intractable, which intractable state may be caused by overexpression of P-gp and/or MRP.

Preferably the intractable condition is a pharmacoresistant condition.

Preferably the intractable condition is a refractory condition.

In an alternative embodiment, the intractable state of the condition is due to the patient's being resistant to treatment with a pharmaceutical which is not a substrate for P-gp or MRP.

Preferably the intractable condition is a pharmacoresistant condition.

Preferably the intractable condition is a refractory condition.

According to another aspect of the invention, there is provided a pharmaceutical composition comprising eslicarbazepine acetate or eslicarbazepine in combination with a drug which reacts adversely with a P-glycoprotein inhibitor or a Multiple Resistant Protein inhibitor, and a pharmaceutically acceptable carrier.

The drug which reacts adversely with a P-glycoprotein inhibitor or a Multiple Resistant Protein inhibitor may be a drug for the treatment of bradycardia; second and third degree atrioventricular block; heart failure; or Wolff-Parkinson-White syndrome; uncontrolled hypertension, premalignant skin lesions or current malignancies, chickenpox and herpes zoster, renal or hepatic impairment, any type of bacterial/viral infection, blood dyscrasias, and uric acid kidney stones.

According to another aspect of the invention, there is provided a pharmaceutical composition comprising eslicarbazepine acetate or eslicarbazepine in combination with a drug for treating one or more of the following conditions: a heart condition, uncontrolled hypertension, premalignant skin lesions or current malignancies, chickenpox and herpes zoster, renal or hepatic impairment, any type of bacterial/viral infection, blood dyscrasias, and uric acid kidney stones, and a pharmaceutically acceptable carrier.

The drug for treating the heart condition may be a drug for the treatment of bradycardia; second and third degree atrioventricular block; heart failure; or Wolff-Parkinson-White syndrome.

The pharmaceutical composition may be formulated in any suitable manner, such as an oral dosage form, such as a tablet or capsule.

It will be appreciated from the foregoing that in accordance with the invention eslicarbazepine or eslicarbazepine acetate may be used to treat a variety of conditions which have previously proved difficult to treat with medicaments that are substrates for P-glycoprotein or Multiple Resistant Proteins.

As used herein, the term treatment and variations such as 'treat' or 'treating' refer to any regime that can benefit a human or non-human animal. The treatment may be in respect of an existing condition or may be prophylactic (preventative treatment). Treatment may include curative, alleviation or prophylactic effects.

In particular, eslicarbazepine and eslicarbazepine acetate are useful to treat patients who suffer from a relapse after treatment with one or more pharmaceutical, i.e. refractory conditions, and also those who are unresponsive to treatment with any pharmaceutical, i.e. pharmacoresistant conditions.

In epilepsy, for example, eslicarbazepine and eslicarbazepine acetate would be useful in the treatment of subjects having more than 4 seizures per week despite with treatment with one or more antiepileptic drug.

In affective disorders such as mania, eslicarbazepine and eslicarbazepine acetate would be useful in the treatment of subjects suffering from a relapse after administration of one or more pharmaceutical which is a P-gp or MRP transporter substrate (e.g. carbamazepine, oxcarbazepine).

In neuropathic pain disorders, eslicarbazepine and eslicarbazepine acetate would be useful in the treatment of subjects suffering from a relapse after administration of one or more analgesic which is P-gp or MRP transporter substrate (e.g. carbamazepine, oxcarbazepine).

It will be appreciated that the invention also encompasses methods of treating the conditions mentioned above, which involve administering a therapeutically effective amount of the active ingredient or ingredients to a subject in need thereof.

The subject treated in accordance with the invention is preferably a human subject.

Medical conditions that can be treated with either eslicarbazepine acetate or S-licarbarzepine with no need for adjunctive therapy with P-gp or MRP blockers include:
 1. Affective disorders
 2. Schizoaffective disorders
 3. Bipolar disorders
 4. Attention disorders
 5. Anxiety disorders
 6. Neuropathic pain and neuropathic pain related disorders
 7. Sensorimotor disorders
 8. Vestibular disorders
 1. Affective disorders include:
 Depression, pre-menstrual dysphoric disorder, post partum depression, post-menopausal depression, anorexia nervosa, bulimia nervosa, and neurodegeneration-related depressive symptoms.
 2. Schizoaffective disorders include:
 Schizodepressive syndromes, schizophrenia, extreme psychotic states, schizomanic syndromes, dysphoric and aggressive behavior, episodic dyscontrol or intermittent explosive disorder, and borderline personality disorder.

3. Bipolar disorders include:

Bipolar disorder and unstable bipolar disorder with rapid fluctuations (rapid cyclers), manic-depressive disorders, acute mania, mood episodes, and manic and hypomanic episodes.

4. Attention disorders include:

Attention deficit hyperactivity disorders and other attention disorders such as autism.

5. Anxiety disorders include:

Social anxiety disorders, post traumatic stress disorder, panic, obsessive compulsive disorder, alcoholism, drug withdrawal syndromes and craving.

6. Neuropathic pain and neuropathic pain related disorders include:

Neuropathic pain and associated hyperalgesia, including trigeminal, herpetic post-herpetic and tabetic neuralgia, diabetic neuropathic pain, migraine, tension-type headache, causalgia, and deafferentation syndromes such as brachial plexus avulsion.

7. Sensorimotor and related disorders disorders include:

Restless legs syndrome, spasticity, hemifacial spasm, nocturnal paroxysmal dystonia, brain ischemia associated motor and sensitive deficits, Parkinson's disease and parkinsonian disorders, antipsychotic-induced motor deficits, tardive dyskinesia, episodic nocturnal wandering and myotonia.

8. Vestibular disorders include:

Tinnitus or other inner ear/cochlear excitability related diseases, including neuronal loss, hearing loss, sudden deafness, vertigo or Meniere's disease.

Methods and Materials

Brain Access of S-Licarbazepine and R-Licarbazepine

CD-1 mice weighing 30-35 g were maintained under controlled environmental conditions (23-24° C.) for at least 5 days before the experiment. All animals interventions were performed in accordance with the European Directive number 86/609, and the rules of the "Guide for the Care and Use of Laboratory Animals", 7th edition, 1996, Institute for Laboratory Animal Research (ILAR), Washington, D.C. In the first series of experiments mice were given by gastric tube S-licarbazepine or R-licarbazepine (350 mg/kg). Blood and brain samples were obtained at 12 different timepoints (15 min, 30 min, 45 min, 1 h, 2 h, 4 h, 6 h, 10 h, 16 h, 24 h, 48 h and 72 h) after drug administration. In the second series of experiments, mice pre-treated with vehicle, verapamil (20 mg/kg) or probenecid (100 mg/kg) were given 30 min later intraperitoneally S-licarbazepine or R-licarbazepine (100 mg/kg). Probenecid has been shown to inhibit both MRP1 and MRP2 (Gerk et al., 2002; Scheffer et al., 2002), but also inhibits organic anion transporters. Although more selective P-gp and MRP1/2 inhibitors exist, verapamil and probenecid are widely used standard inhibitors of these multidrug transporters. After collection of blood, plasma was obtained by centrifugation. Brain samples were homogenised in phosphate buffer (pH 5; 4 mL/g) followed by centrifugation and collection of the supernatant. Plasma and the tissue supernatant were stored frozen until analysis. The assay of S-licarbazepine and R-licarbazepine was performed using a HPLC-UV or LC-MS method following solid phase extraction.

The following pharmacokinetic parameters for S-licarbazepine and R-licarbazepine were derived by non-compartmental analysis from the concentration versus time profiles: maximum observed plasma drug concentration (Cmax), time at which the Cmax occurred (tmax), area under the plasma concentration versus time curve (AUC) from time zero to the last sampling time at which concentrations were at or above the limit of quantification (AUC0-t) and AUC from time zero to infinity (AUC0-∞), elimination half-life (t1/2) and mean residence time (MRT). The pharmacokinetic parameters were determined using WinNonlin (version 4.0). Summary statistics of all data for each treatment and scheduled sampling times were reported, as appropriate, using the geometric mean, arithmetic mean, standard deviation (SD), coefficient of variation (CV), median, minimum and maximum. The statistical package SAS Version 8.2 or higher (SAS Institute, Cary, USA) was used in all computations when considered appropriate.

Kindling Procedure

Vehicle (30% DMSO in distilled water) or the compounds dissolved in 30% DMSO were administered intraperitoneally twice daily. NMRI mice were stimulated twice daily (interstimulation interval 6-7 h) on twelve consecutive days. The electrostimulations with current intensities of 3 mA and duration of 3 s (pulse frequency 50 Hz) were applied via corneally placed saline-soaked copper electrodes. A stimulator was used to deliver a constant current regardless of the impedance of the test object. Seizure severity was ranked according to a modified system of Racine (Racine, 1972): 1, mild facial clonus and eye blinking; 2, severe facial clonus, head nodding, chewing; 3, unilateral or alternating forelimb clonus; 4, bilateral forelimb clonus with rearing and falling; 5, bilateral forelimb clonus with rearing and falling; 6, tonic fore- and/or hindlimb extension.

Formalin Paw Test

The method, which detects analgesic/anti-inflammatory activity, follows that described by Wheeler-Aceto et al (Wheeler-Aceto et al., 1991). NMRI mice were given an intraplantar injection of 5% formalin (25 µl) into the posterior left paw. This treatment induced paw licking in control animals. The time spent licking was counted for 15 minutes, beginning 15 minutes after injection of formalin. 10 mice were studied per group. The test was performed blind. S-Licarbazepine and R-licarbazepine were tested at the dose of 100 mg/kg p.o., administered 120 minutes before the test (i.e. 100 minutes before formalin), and compared with a vehicle control group in each experiment.

Results

Brain Access of S-Licarbazepine and R-Licarbazepine

As depicted in Table 1, both S-licarbazepine and R-licarbazepine are rapidly absorbed after oral administration with Cmax in plasma attained at 15 min (tmax). After the administration of S-licarbazepine only S-licarbazepine is found in plasma, whereas after the administration of R-licarbazepine small amounts of S-licarbazepine were found to be detectable in plasma though the major circulating material is R-licarbazepine (Table 1). Though there are differences in the plasma profiles between S-licarbazepine and R-licarbazepine, it is quite clear that there are similarities for both enantiomers in what concerns their systemic exposure (AUCplasma(S-Licarbazepine)/AUCplasma(R-Licarbazepine)=1.1), elimination half-life (t1/2≈8 h) and mean residence time (MRT≈10-12 h).

In brain, after the administration of S-licarbazepine and R-licarbazepine, the presence respectively of R-licarbazepine and S-licarbazepine is almost negligible (Table 2). This is in line with that observed in plasma. As it would be expected, a comparison of the plasma PK profiles and the brain PK profiles indicates a rightward shift of the brain PK profiles (from 0.25 h to 1.00 h for S-Licarbazepine; from 0.25 h to 0.75 h for R-licarbazepine).

A comparison of the data following the administration of S-licarbazepine with that of R-licarbazepine indicates that the brain ratio AUCbrain(S-Licarbazepine)/AUCbrain(R-Licarbazepine) is 1.9 is greater than that in plasma (AUCplasma(S-Licarbazepine)/AUCplasma(R-Licarbazepine)= 1.1). Thus, it is suggested that distribution of S-licarbazepine into the brain is more favourable than that (almost twice) for R-licarbazepine. However, when other parameters such as half-life and MRT are considered it is apparent that R-Licarbazepine has considerable more difficulty in entry the brain. In fact, as can be observed in FIG. 1, the brain/plasma ratio (considering either Cmax or AUC), the S-licarbazepine brain/plasma ratio was considerably greater than the R-licarbazepine brain/plasma. This clearly indicates that there is stereoselectivity in the process of crossing the blood-brain barrier.

Figure 2:
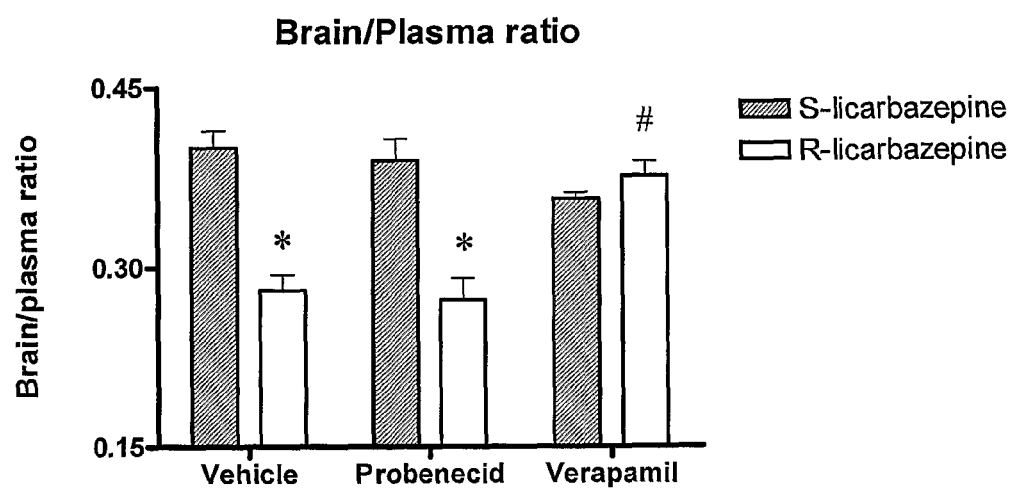
FIG. 2 shows the effect of probenecid and verapimil on the brain plasma ratio for S-licarbazepine and R-licarbazepine.

To assess whether differences in brain penetration of S-licarbazepine and R-licarbazepine were related to susceptibility for efflux through P-gp or MRP, mice were pretreated with verapamil or probenecid. As shown, in FIG. 2, verapamil and probenecid failed to affect the S-licarbazepine brain/plasma ratio. By contrast, verapamil, but not probenecid, markedly increased the R-licarbazepine brain/plasma ratio (FIG. 2). This indicates that S-licarbazepine is not a substrate for both P-gp and MRP, whereas R-licarbazepine is a substrate for P-gp, but not for MRP. It is interesting to underline the fact that the R-licarbazepine brain/plasma ratio after verapamil equals that of S-licarbazepine in vehicle-treated animals (FIG. 2).

Figure 3:
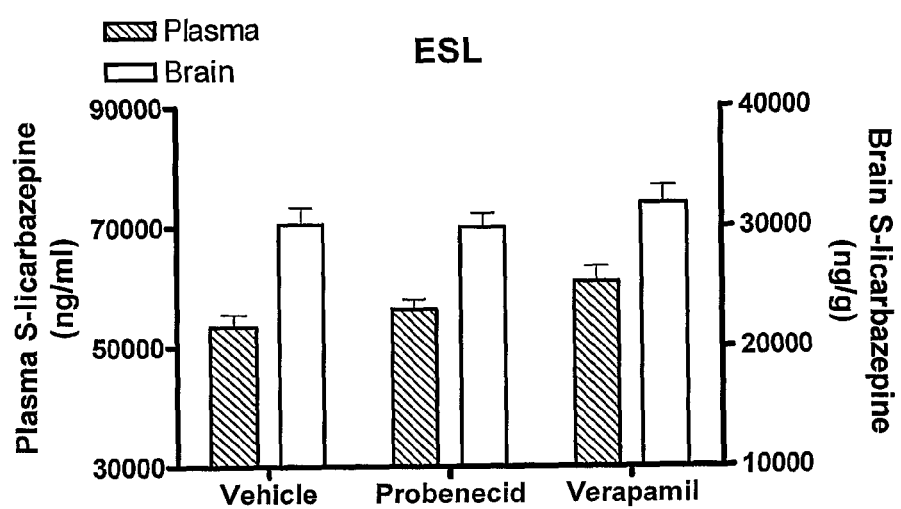
FIG. 3 shows the effect of verapamil and probenecid on the S-licarbazepine brain/plasma ratio after the administration eslicarbazepine acetate.

As shown, in FIG. 3, verapamil and probenecid failed to affect the S-licarbazepine brain/plasma ratio after the administration eslicarbazepine acetate (100 mg/kg, i.p.).

Acquisition of Kindling
Effect of S-Licarbazepine

Figure 4:
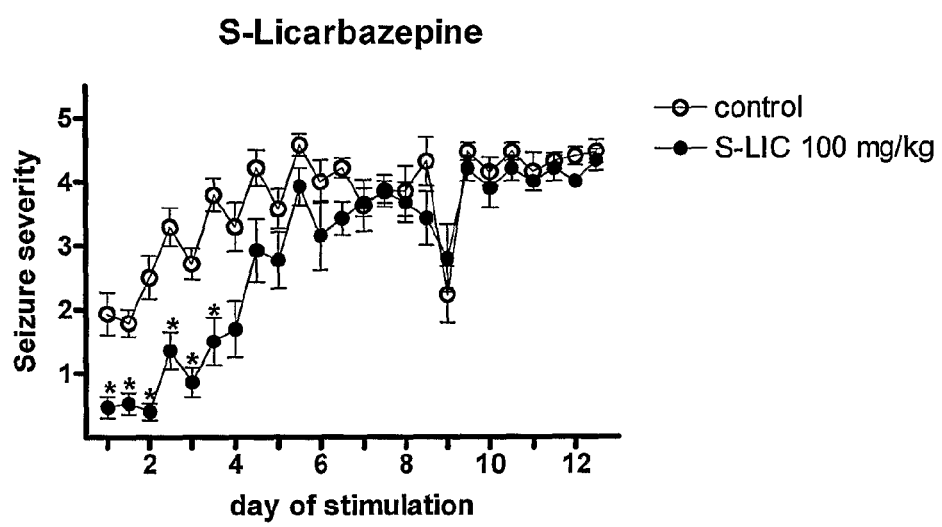
FIG. 4 shows the effect of twice daily treatment with S-licarbazepine on acquisition of kindling.

Twice daily treatment with S-licarbazepine 100 mg/kg exhibited an inhibitory effect on acquisition of kindling (FIG. 4). As compared to the vehicle control group mean seizure severity proved to be significantly lower in the 100 mg/kg S-licarbazepine treatment group at all stimulation sessions of the first three days. The number of stimulations necessary to induce a seizure with a severity score of 3 and 4 was significantly increased in mice that received administrations of S-licarbazepine 100 mg/kg (FIG. 4). When treatment was terminated at day 12 100% of the vehicle-treated animals and all of the treated animals had reached the kindling criterion, i.e. at least one generalized seizure (score 4-6). During the course of the experiment no adverse effects were obvious in S-licarbazepine treated animals.

Effect of R-Licarbazepine

Figure 5:
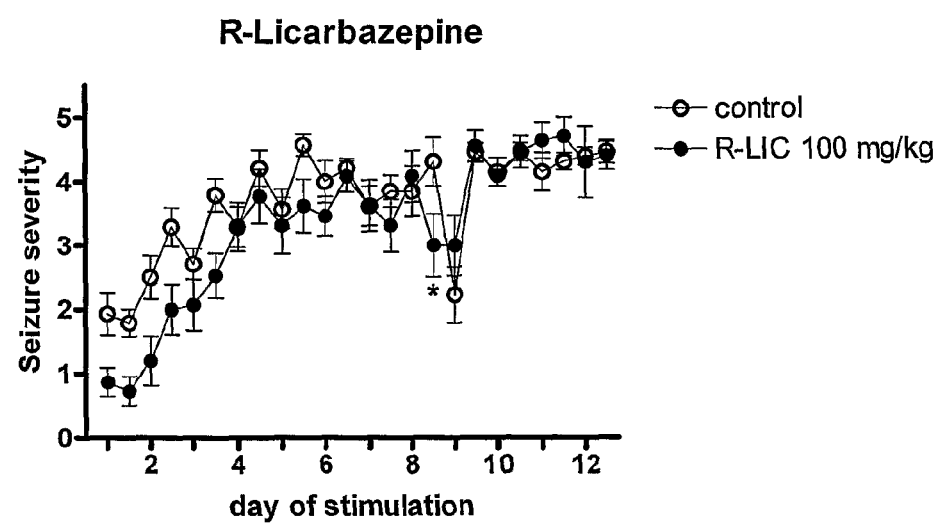
FIG. 5 shows the effect of twice daily treatment with R-licarbazepine on acquisition of kindling.

Twice daily treatment with R-licarbazepine 100 mg/kg exhibited no inhibitory effect on acquisition of kindling (FIG. 5). When seizure severity scores were compared between R-licarbazepine treated animals and control animals, no significant differences were determined except for one stimulation session, i.e. the stimulation in the afternoon of day 8. The number of stimulations necessary to induce a seizure with a severity score of 3, 4, 5, and 6 did not differ between treated mice and control mice (FIG. 5). When treatment was terminated at day 12 100% of the vehicle-treated animals and all of the treated animals had reached the kindling criterion, i.e. at least one generalized seizure (score 4-6). During the course of the experiment no adverse effects were obvious in R-licarbazepine treated animals.

Formalin Paw Test

Figure 6:
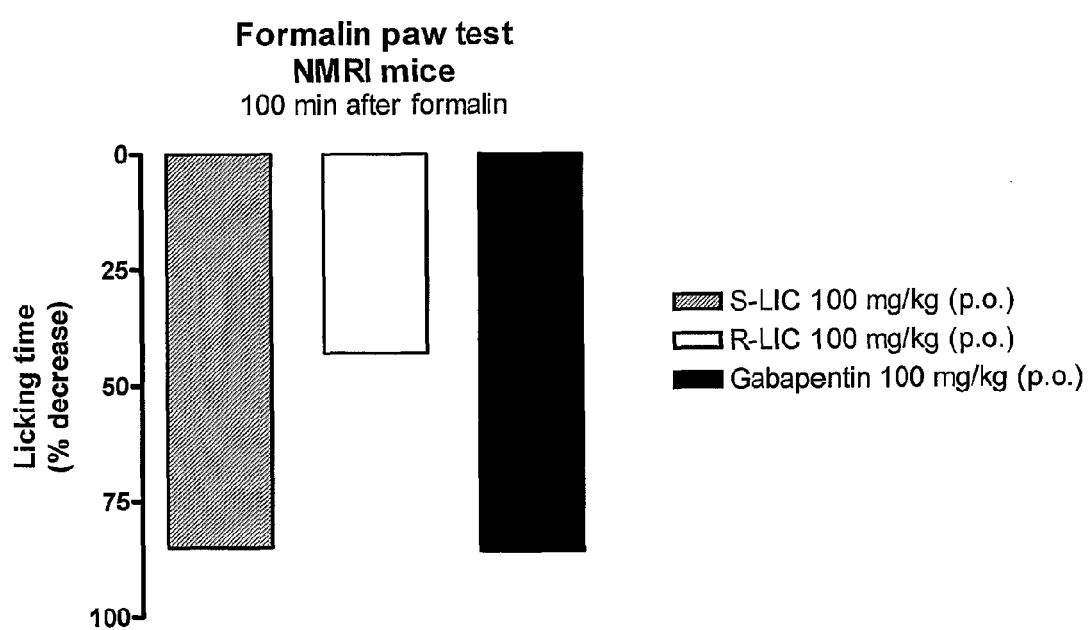
FIG. 6 shows formalin paw test data for S-licarbazepine, R-licarbazepine and gabapentin.

As shown in FIG. 6, S-licarbazepine at 100 mg/kg, administered p.o. 120 minutes before the test (i.e. 100 minutes before formalin), significantly decreased the licking time, as compared with vehicle controls. The decrease in licking time after the administration of R-licarbazepine (100 mg/kg, p.o.) 120 minutes before the test (i.e. 100 minutes before formalin), did not attain statistical significance, as compared with vehicle controls. Gabapentin (100 mg/kg, p.o.), administered 120 minutes before the test (i.e. 100 minutes before formalin) significantly (p<0.05) decreased the licking time, as compared with vehicle controls.

Tables

TABLE 1

Plasma pharmacokinetic (PK) parameters for S-licarbazepine and R-licarbazepine after the oral administration of 350 mg/kg S-licarbazepine or 350 mg/kg R-licarbazepine to CD-1 mice.

| Plasma PK Parameters | after S-Licarbazepine | | after R-Licarbazepine | |
|---|---|---|---|---|
| | S-Lic | R-Lic | S-Lic | R-Lic |
| tmax (h) | 0.25 | NC | 0.25 | 0.25 |
| Cmax (ng/mL) | 41304 | NC | 1024 | 69946 |
| AUC0-t (ng · h/mL) | 186669 | NC | 4582 | 203705 |
| AUC0-∞ (ng · h/mL) | 258278 | NC | NC | 231716 |
| t½ (h) | 7.93 | NC | NC | 8.11 |
| MRT (h) | 11.71 | NC | NC | 10.12 |

NC = not calculated due to absence of measurable concentrations of the analyte.

TABLE 2

Brain pharmacokinetic (PK) parameters for S-licarbazepine and R-licarbazepine after the oral administration of 350 mg/kg S-licarbazepine or 350 mg/kg R-licarbazepine to CD-1 mice.

| Brain PK Parameters | after S-Licarbazepine | | after R-Licarbazepine | |
|---|---|---|---|---|
| | S-Lic | R-Lic | S-Lic | R-Lic |
| tmax (h) | 1.00 | NC | NC | 0.75 |
| Cmax (ng/mL) | 12308 | NC | NC | 8533 |
| AUC0-t (ng · h/mL) | 108610 | NC | NC | 51516 |
| AUC0-∞ (ng · h/mL) | 111302 | NC | NC | 60037 |
| t½ (h) | 4.87 | NC | NC | 7.91 |
| MRT (h) | 7.84 | NC | NC | 11.34 |

NC = not calculated due to absence of measurable concentrations of the analyte.

Discussion

AEDs that fall into the category of P-gp or MRP substrates include all major voltage-gated sodium channel blockers that are the mainstay treatment of monotherapy and adjunctive therapy of patients afflicted with epilepsy, such as phenytoin, phenobarbital, carbamazepine, oxcarbazepine, felbamate and lamotrigine. Levetiracetam is an exception that has been reported not to be a substrate for either P-gp or MRP1/2, as suggested by the finding that neither inhibition of P-gp nor MRP1/MRP2 by verapamil and probenecid, respectively, increased the brain penetration of levetiracetam.

In a recent clinical study in 120 patients with drug-resistant epilepsy who had tried at least 3-4 other AEDs before levetiracetam was instituted, 32% of the patients were seizure-free six months after initiation of levetiracetam therapy (Betts et al., 2003). This impressive and sustainable seizure freedom rate in difficult-to-treat patients under treatment with levetiracetam has been suggested be either a result of a novel mechanism of action as well as the lack of multidrug transporters to limit brain uptake of levetiracetam as suggested by (Potschka et al., 2004).

Eslicarbazepine acetate, administered once-daily, was demonstrated to be very efficacious in partial epilepsy refractory patients (Maia et al., 2004), a characteristic that may relate to the preferential metabolism into S-licarbazepine, escaping drug efflux transporters, such as P-gp and MRP. It should be underlined that approximately 25% became seizure free 1 month after initiation of eslicarbazepine acetate therapy (Almeida et al., 2007).

Advantages of the use of P-gp and/or MRP inhibitors to overcome drug resistance and facilitate access to organs and cells that express high levels of these transporters is still a matter of debate. Though inhibition of P-gp and/or MRP may facilitate drug transfer of P-gp and MRP substrates, it may also compromise safety, since these transport restrict to a major extent the access to a wide range of xenobiotics, some of which are endowed with considerable unwanted effects (Schinkel et al., 2003; Schinkel et al., 1996). Therefore, it is of considerable advantage to use drugs such as eslicarbazepine acetate and S-licarbazepine, which are not substrate for P-gp and/or MRP, rather than use drugs that transported through transporters, such as R-licarbazepine, phenytoin, phenobarbital, carbamazepine, oxcarbazepine, felbamate and lamotrigine, in combination with P-gp and/or MRP inhibitors.

REFERENCES

Abbott, N. J. (2002). Mechanisms of Drug Resistance in Epilepsy: Lessons from Oncology. ed Ling, V. pp. 38-46. Chichester: Wiley.

Almeida, L., Falcao, A., Maia, J., Mazur, D., Gellert, M. & Soares-da-Silva, P. (2005a). Single-dose and steady-state pharmacokinetics of eslicarbazepine acetate (BIA 2-093) in healthy elderly and young subjects. J Clin Pharmacol, 45, 1062-6.

Almeida, L., Falcão, A., Maia, J., Mazur, D., Gellert, M. & Soares-da-Silva, P. (2005b). Effect of gender on the pharmacokinetics of eslicarbazepine acetate (BIA 2-093), a new voltage-gated sodium channel inhibitor. Epilepsia, 46, 282-283.

Almeida, L., Silveira, P., Vaz-da-Silva, M. & Soares-da-Silva, P. (2002). Pharmacokinetic profile of BIA 2-093, a putative new antiepileptic drug, after single and multiple administration in human healthy volunteers. Epilepsia, 43, 146-147.

Almeida, L. & Soares-da-Silva, P. (2003). Safety, tolerability and pharmacokinetic profile of BIA 2-093, a novel putative antiepileptic agent, during first administration to humans. Drugs R D, 4, 269-84.

Almeida, L. & Soares-da-Silva, P. (2004). Safety, tolerability, and pharmacokinetic profile of BIA 2-093, a novel putative antiepileptic, in a rising multiple-dose study in young healthy humans. J Clin Pharmacol, 44, 906-18.

Aronica, E., Gorter, J. A., Jansen, G. H., van Veelen, C. W., van Rijen, P. C., Leenstra, S., Ramkema, M., Scheffer, G. L., Scheper, R. J. & Troost, D. (2003). Expression and cellular distribution of multidrug transporter proteins in two major causes of medically intractable epilepsy: focal cortical dysplasia and glioneuronal tumors. Neuroscience, 118, 417-429.

Aronica, E., Gorter, J. A., Ramkema, M., Redeker, S., Ozbas-Gerceker, F., van Vliet, E. A., Scheffer, G. L., Scheper, R. J., van der Valk, P., Baayen, J. C. & Troost, D. (2004). Expression and cellular distribution of multidrug resistance-related proteins in the hippocampus of patients with mesial temporal lobe epilepsy. Epilepsia, 45, 441-451.

Benes, J., Parada, A., Figueiredo, A. A., Alves, P. C., Freitas, A. P., Learmonth, D. A., Cunha, R. A., Garrett, J. & Soares-da-Silva, P. (1999). Anticonvulsant and sodium channel-blocking properties of novel 10,11-dihydro-5H-dibenz[b,f]azepine-5-carboxamide derivatives. J Med Chem, 42, 2582-2587.

Betts, T., Yarrow, H., Greenhill, L. & Barrett, M. (2003). Clinical experience of marketed Levetiracetam in an epilepsy clinic—a one year follow up study. Seizure, 12, 136-140.

Bialer, M., Johannessen, S., Kupferberg, Levy, R., Loiseau, P. & Perucca, E. (2004). Progress report on new antiepileptic drugs: a summary of the Seventh EILAT Conference (EILAT VII). Epilepsy Research, 61, 1-48.

Clinckers, R., Smolders, I., Meurs, A., Ebinger, G. & Michotte, Y. (2005). Quantitative in vivo microdialysis study on the influence of multidrug transporters on the blood-brain barrier passage of oxcarbazepine: concomitant use of hippocampal monoamines as pharmacodynamic markers for the anticonvulsant activity. J Pharmacol Exp Ther, 314, 725-731.

Dombrowski, S. M., Desai, S. Y., Marroni, M., Cucullo, L., Goodrich, K., Bingaman, W., Mayberg, M. R., Bengez, L. & Janigro, D. (2001). Overexpression of multiple drug resistance genes in endothelial cells from patients with refractory epilepsy. Epilepsia, 42, 1501-1506.

Faigle, J. W. & Menge, G. P. (1990). Metabolic characteristics of oxcarbazepine and their clinical significance: comparison with carbamazepine. Behav Neurol, 3 (Suppl 1), 21-30.

Feldmann, K. F., Brechbühler, S., Faigle, J. W. & Imhof, P. (1978). Pharmacokinetics and metabolism of GP 47 680, a compound related to carbamazepine, in animals and man. In Advances in Epileptology. eds Meinardi, H. & Rowan, A. J. pp. 290-294. Amsterdam/Lisse: Swets & Zeitlinger.

Feldmann, K. F., Dörrhöfer, G., Faigle, J. W. & Imhof, P. (1981). Pharmacokinetics and metabolism of GP 47 779, the main human metabolite of oxcarbazepine (GP 47 680) in animals and healthy volunteers. In Advances in Epileptology: XIIth Epilepsy Intern. Symp. ed Dam, M. pp. 89-96. New York: Raven Press.

Flesch, G., Francotte, E., Hell, F. & Degen, P. H. (1992). Determination of the R-(−) and S-(+) enantiomers of the monohydroxylated metabolite of oxcarbazepine in human plasma by enantioselective high-performance liquid chromatography. J Chromatogr, 581, 147-151.

Gerk, P. M. & Vore, M. (2002). Regulation of expression of the multidrug resistance-associated protein 2 (MRP2) and its role in drug disposition. J Pharmacol Exp Ther, 302, 407-415.

Kortekaas, R., Leenders, K. L., van Oostrom, J. C., Vaalburg, W., Bart, J., Willemsen, A. T. & Hendrikse, N. H. (2005). Blood-brain barrier dysfunction in parkinsonian midbrain in vivo. Ann Neurol, 57, 176-179.

Kwan, P. & Brodie, M. J. (2000). Early identification of refractory epilepsy. N Engl J Med 342, 314-319.

Kwan, P. & Brodie, M. J. (2005). Potential role of drug transporters in the pathogenesis of medically intractable epilepsy. Epilepsia, 46, 224-235.

Löscher, W. & Potschka, H. (2005a). Drug resistance in brain diseases and the role of drug efflux transporters. Nat Rev Neurosci, 6, 591-602.

Löscher, W. & Potschka, H. (2005b). Role of drug efflux transporters in the brain for drug disposition and treatment of brain diseases. Prog Neurobiol, 76, 22-26.

Löscher, W. & Schmidt, D. (2004). New horizons in the development of antiepileptic drugs: the search for new targets. Epilepsy Res, 60, 77-150.

Maia, J., Almeida, L. & Soares-da-Silva, P. (2004). BIA 2-093 as add-on therapy for refractory partial epilepsy in adults. Epilepsia, 45, 158.

Marchi, N., Guiso, G., Rizzi, M., Pirker, S., Novak, K., Czech, T., Baumgartner, C., Janigro, D., Caccia, S. & Vezzani, A. (2005). A pilot study on brain-to-plasma partition of 10,11-dyhydro-10-hydroxy-5H-dibenzo(b,f)azepine-5-carboxamide and MDR1 brain expression in epilepsy patients not responding to oxcarbazepine. Epilepsia, 46, 1613-1620.

Marchi, N., Hallene, K. L., Kight, K. M., Cucullo, L., Moddel, G., Bingaman, W., Dini, G., Vezzani, A. & Janigro, D. (2004). Significance of MDR1 and multiple drug resistance in refractory human epileptic brain. BMC Med, 2, 37.

May, T. W., Korn-Merker, E. & Rambeck, B. (2003). Clinical pharmacokinetics of oxcarbazepine. Clin Pharmacokinet 42, 1023-1042.

Mohanraj, R. & Brodie, M. J. (2005). Pharmacological outcomes in newly diagnosed epilepsy. Epilepsy Behav, 6, 382-387.

Potschka, H., Baltes, S. & Löscher, W. (2004). Inhibition of multidrug transporters by verapamil or probenecid does not alter blood-brain barrier penetration of levetiracetam in rats. Epilepsy Res, 58, 85-91.

Potschka, H., Fedrowitz, M. & Löscher, W. (2002). P-Glycoprotein-mediated efflux of phenobarbital, lamotrigine, and felbamate at the blood brain barrier: evidence from microdialysis experiments in rats. Neurosci Lett 327, 173-176.

Potschka, H., Fedrowitz, M. & Löscher, W. (2001a). P-glycoprotein and multidrug resistance-associated protein are involved in the regulation of extracellular levels of the major antiepileptic drug carbamazepine in the brain. Neuroreport 12, 3557-3560.

Potschka, H., Fedrowitz, M. & Löscher, W. (2003). Multidrug resistance protein MRP2 contributes to blood-brain barrier function and restricts antiepileptic drug activity. J Pharmacol Exp Ther, 306, 124-131.

Potschka, H. & Löscher, W. (2001b). In vivo evidence for P-glycoprotein mediated transport of phenytoin at the blood-brain barrier of rats. Epilepsia, 42, 1231-1240.

Racine, R. J. (1972). Modification of seizure activity by electrical stimulation: II. Motor seizure. Electroencephalograph. Clin Neurophys, 32, 295-299.

Rizzi, M., Caccia, S., Guiso, G., Richichi, C., Gorter, J. A., Aronica, E., Aliprandi, M., Bagnati, R., Fanelli, R., D'Incalci, M., Samanin, R. & Vezzani, A. (2002). Limbic seizures induce Pglycoprotein in rodent brain: functional implications for pharmacoresistance. J Neurosci, 22, 5833-5839.

Scheffer, G. L. & Scheper, R. J. (2002). Drug resistance molecules: lessons from oncology. Novartis. Found. Symp., 243, 19-31.

Schinkel, A. H. & Jonker, J. W. (2003). Mammalian drug efflux transporters of the ATP binding cassette (ABC) family: an overview. Adv Drug Deliv Rev, 55, 3-29.

Schinkel, A. H., Wagenaar, E., Mol, C. A. & van Deemter, L. (1996). P-glycoprotein in the blood-brain barrier of mice influences the brain penetration and pharmacological activity of many drugs. J Clin Invest., 97, 2517-2524.

Schmidt, D., Arroyo, S., Baulac, M., Dam, M., Dulac, O., Friis, M. L., Kalviainen, R., Kramer, G., van Parys, J., Pedersen, B. & Sachdeo, R. (2001). Recommendations on the clinical use of oxcarbazepine in the treatment of epilepsy: a consensus view. Acta Neurol Scand, 104, 167-170.

Schmidt, D. & Löscher, W. (2005). Drug resistance in epilepsy: putative neurobiologic and clinical mechanisms. Epilepsia 46, 858-877.

Schutz, H., Feldmann, K. F., Faigle, J. W., Kriemler, H. P. & Winkler, T. (1986). The metabolism of 14C-oxcarbazepine in man. Xenobiotica, 16, 769-778.

Shorvon, S. (2000). Oxcarbazepine: a review. Seizure, 9, 75-79.

Sills, G. J., Kwan, P., Butler, E., de Lange, E. C., van den Berg, D. J. & Brodie, M. J. (2002). P-glycoprotein-mediated efflux of antiepileptic drugs: preliminary studies in mdr1a knockout mice. Epilepsy Behav, 3, 427-432.

Sisodiya, S. M. (2003). Mechanisms of antiepileptic drug resistance. Curr Opin. Neurol., 16, 197-201.

Sisodiya, S. M., Lin, W.-R., Harding, B. N., Squier, M. V., Keir, G. & Thom, M. (2002). Drug resistance in epilepsy: expression of drug resistance proteins in common causes of refractory epilepsy. Brain, 125, 22-31.

Soares-da-Silva, P. (2004). BIA 2-093. Epilepsy Research, 61, 4-6.

Sperling, M. R. (2004). The consequences of uncontrolled epilepsy. CNS Spectr, 9, 98-99.

Stephen, L. J., Kelly, K., Mohanraj, R. & Brodie, M. J. (2006). Pharmacological outcomes in older people with newly diagnosed epilepsy. Epilepsy Behav, 8, 434-437.

Summers, M. A., Moore, J. L. & McAuley, J. W. (2004). Use of verapamil as a potential P-glycoprotein inhibitor in a patient with refractory epilepsy. Ann. Pharmacother, 38, 1631-1634.

Tartara, A., Galimberti, C. A., Manni, R., Morini, R., Limido, G., Gatti, G., Barton, A., Strada, G. & Perucca, E. (1993). The pharmacokinetics of oxcarbazepine and its active metabolite 10-hydroxy-carbazepine in healthy subjects and in epileptic patients treated with phenobarbitone or valproic acid. Br J Clin Pharmacol, 36, 366-368.

Tishler, D. M., Weinberg, K. I., Hinton, D. R., Barbaro, N., Annett, G. M. & Raffel, C. (1995). MDR1 gene expression in brain of patients with medically intractable epilepsy. Epilepsia, 36, 1-6.

van Vliet, E., Aronica, E., Redeker, S., Marchi, N., Rizzi, M., Vezzani, A. & Gorter, J. A. (2004). Selective and persistent upregulation of mdr1b mRNA and P-glycoprotein in the parahippocampal cortex of chronic epileptic rats. Epilepsy Res, 60, 203-213.

Volk, H. A., Burkhardt, K., Potschka, H., Chen, J., Becker, A. & Löscher, W. (2004a). Neuronal expression of the drug efflux transporter P-glycoprotein in the rat hippocampus after limbic seizures. Neuroscience, 123, 751-759.

Volk, H. A., Potschka, H. & Löscher, W. (2004b). Increased expression of the multidrug transporter P-glycoprotein in limbic brain regions after amygdala-kindled seizures in rats. Epilepsy Res, 58, 67-79.

Volosov, A., Xiaodong, S., Perucca, E., Yagen, B., Sintov, A. & Bialer, M. (1999). Enantioselective pharmacokinetics of 10-hydroxycarbazepine after oral administration of oxcarbazepine to healthy Chinese subjects. Clin Pharmacol Ther, 66, 547-553.

Wheeler-Aceto, H. & Cowan, A. (1991). Standardization of the rat paw formalin test for the evaluation of analgesics. Psychopharmacology (Berl), 104, 35-44.

What is claimed is:
1. A method for treating an intractable epilepsy condition comprising administering to a subject in need thereof a therapeutically effective amount of eslicarbazepine or eslicarbazepine acetate wherein the subject has previously been treated with oxcarbazepine.

2. The method according to claim 1, wherein the subject is under 2 years of age.

3. The method according to claim 1, wherein the eslicarbazepine or eslicarbazepine acetate is administered in the absence of a P-glycoprotein inhibitor or a Multiple Resistant Protein inhibitor.

4. The method according to claim 1, wherein the intractable state of the condition is due to overexpression of P-glycoprotein and/or Multiple Resistant Protein.

5. The method according to claim 1, wherein the intractable condition is a pharmacoresistant condition.

6. The method according to claim 1, wherein the intractable condition is a refractory condition.

7. The method according to claim 1, wherein the subject suffers from a relapse after treatment with at least one pharmaceutical composition.

8. The method according to claim 1, wherein the subject is a partial epilepsy refractory patient.

9. The method according to claim 1, wherein the subject has not become seizure-free despite treatment with two or more anti-epileptic drugs.

10. The method according to claim 9, wherein the subject has not become seizure-free despite treatment with two or more anti-epileptic drugs administered at their maximal tolerated dose.

11. The method according to claim 1, wherein the subject has become increasingly less responsive to medication and suffers from an increasing number of seizures.

12. The method according to claim 1, wherein the subject has at least 4 seizures per week despite treatment with at least one anti-epileptic drug.

13. The method according to claim 1, wherein the subject is a patient with drug-resistant epilepsy who has tried at least 3-4 other anti-epileptic drugs.

14. The method according to claim 6, wherein the refractory state of the condition is due to over-expression of P-glycoprotein and/or Multiple Resistant Proteins.

15. The method according to claim 1, wherein the medicament that is a substrate for P-glycoprotein or Multiple Resistant Proteins is oxcarbazepine.

16. The method according to claim 1, wherein the subject is administered with a therapeutically effective amount of eslicarbazepine acetate.

17. The method according to claim 1, wherein the subject is administered with a therapeutically effective amount of eslicarbazepine.

18. The method according to claim 1, wherein the epilepsy is temporal lobe epilepsy.

19. The method according to claim 1, wherein the therapeutically effective amount of eslicarbazepine or eslicarbazepine acetate is administered as adjunctive therapy to a subject being treated with at least one other anti-epileptic drug.

20. The method according to claim 1, wherein the subject has previously been treated with a pharmaceutical composition comprising at least one inhibitor of P-glycoprotein or Multiple Resistant Protein.

21. A method for treating an intractable epilepsy condition comprising administering to a subject in need thereof a therapeutically effective amount of eslicarbazepine or eslicarbazepine acetate wherein the subject has previously been treated with oxcarbazepine, and wherein the eslicarbazepine or eslicarbazepine acetate is administered as a monotherapy for treating said condition.

22. The method according to claim 21, wherein the eslicarbazepine or eslicarbazepine acetate is administered in the absence of a P-glycoprotein inhibitor or a Multiple Resistant Protein inhibitor.

23. The method according to claim 21, wherein the intractable state of the condition is due to overexpression of P-glycoprotein and/or Multiple Resistant Protein.

24. The method according to claim 21, wherein the intractable condition is a pharmacoresistant condition.

25. The method according to claim 21, wherein the intractable condition is a refractory condition.

26. The method according to claim 21, further comprising diagnosing the patient at having an intractable epilepsy condition.

27. The method according to claim 21, wherein the subject is administered with a therapeutically effective amount of eslicarbazepine acetate.

28. The method according to claim 21, wherein the subject is administered with a therapeutically effective amount of eslicarbazepine.

* * * * *

UNITED STATES PATENT AND TRADEMARK OFFICE
CERTIFICATE OF CORRECTION

PATENT NO. : 9,763,954 B2
APPLICATION NO. : 14/134843
DATED : September 19, 2017
INVENTOR(S) : Patricio Manuel Vieira Araújo Soares Da Silva Page 1 of 5

It is certified that error appears in the above-identified patent and that said Letters Patent is hereby corrected as shown below:

On the Title Page

Below Abstract, Should read 27 Claims, 5 Drawings Sheets

In the Claims

Column 16, Line 63 to Column 18, Line 41, delete Claims 1-28:

"1. A method for treating an intractable epilepsy condition comprising administering to a subject in need thereof a therapeutically effective amount of eslicarbazepine or eslicarbazepine acetate wherein the subject has previously been treated with oxcarbazepine.

2. The method according to claim 1, wherein the subject is under 2 years of age.

3. The method according to claim 1, wherein the eslicarbazepine or eslicarbazepine acetate is administered in the absence of a P-glycoprotein inhibitor or a Multiple Resistant Protein inhibitor.

4. The method according to claim 1, wherein the intractable state of the condition is due to overexpression of P-glycoprotein and/or Multiple Resistant Protein.

5. The method according to claim 1, wherein the intractable condition is a pharmacoresistant condition.

6. The method according to claim 1, wherein the intractable condition is a refractory condition.

7. The method according to claim 1, wherein the subject suffers from a relapse after treatment with at least one pharmaceutical composition.

8. The method according to claim 1, wherein the subject is a partial epilepsy refractory patient.

Signed and Sealed this
Sixth Day of August, 2019

Andrei Iancu
*Director of the United States Patent and Trademark Office*

9. The method according to claim 1, wherein the subject has not become seizure-free despite treatment with two or more anti-epileptic drugs.

10. The method according to claim 9, wherein the subject has not become seizure-free despite treatment with two or more anti-epileptic drugs administered at their maximal tolerated dose.

11. The method according to claim 1, wherein the subject has become increasingly less responsive to medication and suffers from an increasing number of seizures.

12. The method according to claim 1, wherein the subject has at least 4 seizures per week despite treatment with at least one anti-epileptic drug.

13. The method according to claim 1, wherein the subject is a patient with drug-resistant epilepsy who has tried at least 3-4 other anti-epileptic drugs.

14. The method according to claim 6, wherein the refractory state of the condition is due to over-expression of P-glycoprotein and/or Multiple Resistant Proteins.

15. The method according to claim 1, wherein the medicament that is a substrate for P-glycoprotein or Multiple Resistant Proteins is oxcarbazepine.

16. The method according to claim 1, wherein the subject is administered with a therapeutically effective amount of eslicarbazepine acetate.

17. The method according to claim 1, wherein the subject is administered with a therapeutically effective amount of eslicarbazepine.

18. The method according to claim 1, wherein the epilepsy is temporal lobe epilepsy.

19. The method according to claim 1, wherein the therapeutically effective amount of eslicarbazepine or eslicarbazepine acetate is administered as adjunctive therapy to a subject being treated with at least one other anti-epileptic drug.

20. The method according to claim 1, wherein the subject has previously been treated with a pharmaceutical composition comprising at least one inhibitor of P-glycoprotein or Multiple Resistant Protein.

21. A method for treating an intractable epilepsy condition comprising administering to a subject in need thereof a therapeutically effective amount of eslicarbazepine or eslicarbazepine acetate wherein the subject has previously been treated with oxcarbazepine, and wherein the eslicarbazepine or eslicarbazepine acetate is administered as a monotherapy for treating said condition.

22. The method according to claim 21, wherein the eslicarbazepine or eslicarbazepine acetate is administered in the absence of a P-glycoprotein inhibitor or a Multiple Resistant Protein inhibitor.

23. The method according to claim 21, wherein the intractable state of the condition is due to overexpression of P-glycoprotein and/or Multiple Resistant Protein.

24. The method according to claim 21, wherein the intractable condition is a pharmacoresistant condition.

25. The method according to claim 21, wherein the intractable condition is a refractory condition.

26. The method according to claim 21, further comprising diagnosing the patient at having an intractable epilepsy condition.

27. The method according to claim 21, wherein the subject is administered with a therapeutically effective amount of eslicarbazepine acetate.

28. The method according to claim 21, wherein the subject is administered with a therapeutically effective amount of eslicarbazepine."

And insert therefor:

--1. A method for treating an intractable epilepsy condition comprising administering to a subject in need thereof a therapeutically effective amount of eslicarbazepine or eslicarbazepine acetate wherein the subject has previously been treated with oxcarbazepine.

2. The method according to claim 1, wherein the subject is under 2 years of age.

3. The method according to claim 1, wherein the eslicarbazepine or eslicarbazepine acetate is administered in the absence of a P-glycoprotein inhibitor or a Multiple Resistant Protein inhibitor.

4. The method according to claim 1, wherein the intractable state of the condition is due to overexpression of P-glycoprotein and/or Multiple Resistant Protein.

5. The method according to claim 1, wherein the intractable condition is a pharmacoresistant condition.

6. The method according to claim 1, wherein the intractable condition is a refractory condition.

7. The method according to claim 1, wherein the subject suffers from a relapse after treatment with at least one pharmaceutical composition.

8. The method according to claim 1, wherein the subject is a partial epilepsy refractory patient.

9. The method according to claim 1, wherein the subject has not become seizure-free despite treatment with two or more anti-epileptic drugs.

10. The method according to claim 9, wherein the subject has not become seizure-free despite treatment with two or more anti-epileptic drugs administered at their maximal tolerated dose.

11. The method according to claim 1, wherein the subject has become increasingly less responsive to medication and suffers from an increasing number of seizures.

12. The method according to claim 1, wherein the subject has at least 4 seizures per week despite treatment with at least one anti-epileptic drug.

13. The method according to claim 1, wherein the subject is a patient with drug-resistant epilepsy who has tried at least 3-4 other anti-epileptic drugs.

14. The method according to claim 6, wherein the refractory state of the condition is due to over-expression of P-glycoprotein and/or Multiple Resistant Proteins.

15. The method according to claim 1, wherein the subject is administered with a therapeutically effective amount of eslicarbazepine acetate.

16. The method according to claim 1, wherein the subject is administered with a therapeutically effective amount of eslicarbazepine.

17. The method according to claim 1, wherein the epilepsy is temporal lobe epilepsy.

18. The method according to claim 1, wherein the therapeutically effective amount of eslicarbazepine or eslicarbazepine acetate is administered as adjunctive therapy to a subject being treated with at least one other anti-epileptic drug.

19. The method according to claim 1, wherein the subject has previously been treated with a pharmaceutical composition comprising at least one inhibitor of P-glycoprotein or Multiple Resistant Protein.

20. A method for treating an intractable epilepsy condition comprising administering to a subject in need thereof a therapeutically effective amount of eslicarbazepine or eslicarbazepine acetate wherein the subject has previously been treated with oxcarbazepine, and wherein the eslicarbazepine or eslicarbazepine acetate is administered as a monotherapy for treating said condition.

21. The method according to claim 20, wherein the eslicarbazepine or eslicarbazepine acetate is administered in the absence of a P-glycoprotein inhibitor or a Multiple Resistant Protein inhibitor.

22. The method according to claim 20, wherein the intractable state of the condition is due to overexpression of P-glycoprotein and/or Multiple Resistant Protein.

23. The method according to claim 20, wherein the intractable condition is a pharmacoresistant condition.

24. The method according to claim 20, wherein the intractable condition is a refractory condition.

25. The method according to claim 20, further comprising diagnosing the patient at having an intractable epilepsy condition.

26. The method according to claim 20, wherein the subject is administered with a therapeutically effective amount of eslicarbazepine acetate.

27. The method according to claim 20, wherein the subject is administered with a therapeutically effective amount of eslicarbazepine.--